US007838522B2

(12) United States Patent
Esposito et al.

(10) Patent No.: US 7,838,522 B2
(45) Date of Patent: Nov. 23, 2010

(54) BENZOTHIAZOLE FORMULATIONS AND USE THEREOF

(75) Inventors: Pierandrea Esposito, Ivrea (IT); Daniela Chicco, Albiano d'Ivrea (IT); Luca Donati, Porto San Giorgio (IT); Andrea Leonardi, Saint Genis Pouilly (FR); Stefania Bertero, Saint Julien en Genevois (FR); Jean-Pierre Gotteland, Beaumont (FR); Pascale Gaillard, Collonges sous Saleve (FR); Isabelle Jeanclaude-Etter, Bellevue (CH); Simone Grandolini, Brufa di Torgiano (IT); Mario Maio, Tivoli (IT)

(73) Assignee: Ares Trading S.A., Aubonne (CH)

( * ) Notice: Subject to any disclaimer, the term of this patent is extended or adjusted under 35 U.S.C. 154(b) by 129 days.

(21) Appl. No.: 11/667,802

(22) PCT Filed: Nov. 16, 2005

(86) PCT No.: PCT/EP2005/056020

§ 371 (c)(1),
(2), (4) Date: Aug. 16, 2007

(87) PCT Pub. No.: WO2006/053882

PCT Pub. Date: May 26, 2006

(65) Prior Publication Data

US 2008/0051397 A1 Feb. 28, 2008

Related U.S. Application Data

(60) Provisional application No. 60/628,998, filed on Nov. 18, 2004.

(30) Foreign Application Priority Data

Nov. 17, 2004 (EP) .................................. 04105843

(51) Int. Cl.
*A61K 31/5377* (2006.01)
*A61K 31/428* (2006.01)
*C07D 413/14* (2006.01)
*C07D 277/62* (2006.01)

(52) U.S. Cl. ................. 514/233.8; 514/235.8; 514/367; 544/122; 548/152

(58) Field of Classification Search .............. 514/233.8, 514/235.8, 367; 544/122; 548/152
See application file for complete search history.

(56) References Cited

U.S. PATENT DOCUMENTS 4,988,679 A 1/1991 Chavkin et al.
5,433,951 A 7/1995 Serajuddin et al.
5,540,938 A 7/1996 Masterson et al.
2006/0177509 A1* 8/2006 Nagahara et al. ............ 424/470

FOREIGN PATENT DOCUMENTS

| EP | 0727406 B1 | 8/1996 |
|---|---|---|
| WO | WO 98/48802 | 11/1998 |
| WO | WO 99/55678 | 11/1999 |
| WO | WO 99/67230 | 12/1999 |
| WO | WO 01/45698 A1 | 6/2001 |
| WO | WO 01/47920 A1 | 7/2001 |
| WO | WO 02/28866 A2 | 4/2002 |
| WO | WO 03/047570 A1 | 6/2003 |
| WO | WO 03/070711 A1 | 8/2003 |
| WO | WO 03/091249 A1 | 11/2003 |
| WO | WO 2004/028251 A1 | 4/2004 |
| WO | WO 2004/043965 A1 | 5/2004 |
| WO | WO 2005/025567 * | 3/2005 |
| WO | WO 2005/049192 A1 | 6/2005 |

OTHER PUBLICATIONS

Jadhav et al. [Gelucires: Pharmaceutical Applications, Pharmainfo. net 6(4) (2008) 1-11].*
Golub et al. Science (1999), vol. 286 531-537.*
Lala et al. Cancer and Metastasis Reviews (1998), 17(1), 91-106.*
Aungst, B., et al., "Improved Oral Bioavailability of an HIV Protease Inhibitor Using Gelucire 44/14 and Labrasol Vehicles," *Bull. Tech. Gattefossé*, 87: 49-54 (1994).
Bruner-Tran, K., et al., "Experimental Endometriosis: The Nude Mouse as a Xenographic Host," *Annals New York Academy of Sciences*, 955: 328-339 (2002).
Chabaka, L., et al., "Facile Synthesis of 2-Furyl-, 2-Pyrrolyl-, 2-Imidazolyl—and Pyrrolo-Azoles from 2-Substituted Methylazoles," *Polish Journal of Chemistry*, 68: 1317-1325 (1994).
D'Antonio, M., et al., "Ability of Recombinant Human TNF Binding Protein-1 (r-hTBP-1) to Inhibit the Development of Experimentally-Induced Endometriosis in Rats," *Journal of Reproductive Immunology*, 48: 81-98 (2000).
International Search Report for International Application No. PCT/EP2005/056020 dated Jun. 7, 2006.
Written Opinion of the International Searching Authority, International Application No. PCT/EP2005/056020 dated Jun. 7, 2006.
Notification Concerning Transmittal of International Preliminary Report on Patentability, and International Preliminary Report on Patentability, International Application No. PCT/EP2005/056020, mail date May 22, 2007.

* cited by examiner

*Primary Examiner*—Golam M. M. Shameem
*Assistant Examiner*—Samantha L Shterengarts
(74) *Attorney, Agent, or Firm*—Hamilton, Brook, Smith, Reynolds, P.C.

(57) ABSTRACT

The present invention is related to macrogol glyceride pharmaceutical formulations containing benzothiazole derivatives. In particular, the invention is related to benzothiazole stearoyl macrogol pharmaceutical formulations, method of preparation and use thereof.

22 Claims, 7 Drawing Sheets

Formulation (6)

Formulation (2)

BENZOTHIAZOLE FORMULATIONS AND USE THEREOF

RELATED APPLICATIONS

This application is the U.S. National Stage of International Application No. PCT/EP2005/056020, filed Nov. 16, 2005, published in English, and claims priority under 35 U.S.C. §119 or 365 to European Application No. 04105843.9, filed Nov. 17, 2004 and U.S. Provisional Application No. 60/628,998, filed Nov. 18, 2004.

FIELD OF THE INVENTION

The present invention relates to macrogol glyceride pharmaceutical formulations containing benzothiazole derivatives. In particular, the invention relates to stearoyl macrogol glyceride formulations of benzothiazole derivatives, method of preparation and use thereof.

BACKGROUND OF THE INVENTION

Macrogol glycerides, i.e. saturated polyglycolized glycerides are "Gelucire® type" excipients. Gelucires® are semi-solid excipients which are prepared by the alcoholysis of natural oils with polyoxyethylene glycols. Gelucires® are a mixture of mono-, di- and triglycerides (fatty acid esters of glycerol) and mono- and di-fatty acid esters of polyethylene glycol (PEG or macrogol). Fatty acid esters of glycerol and PEG esters present in Gelucires® are from long chains fatty acids ($C_{12}$ to $C_{18}$).

The large family of Gelucires® is characterized by a wide range of melting points of from about 33° C. to about 64° C. and by a hydrophilic lipophilic balance (HLB) of from about 1 to about 14.

The nature and proportion of each component are specific to a specific grade of Gelucires®. The grade of Gelucires® is designated by two numbers separated by a slash, the first number indicating its melting point and the second, the HLB.

Gelucires® have been used as excipients in different formulations such as in formulations of Theophilline (U.S. Pat. No. 4,988,679), Captopril (U.S. Pat. No. 5,433,951) or an HIV protease inhibitor (Aungst et al., 1994, *Bull. Tech. Gattefossé*, 87, 49-54).

Commercially available Gelucires® comprise Gelucire® 44/14, Gelucire® 50/13, Gelucire® 53/10, Gelucire® 50/02, Gelucire® 54/02 (also available as Precirol®), Gelucire® 62/05, Gelucire® 64/02 (also available as Precirol® WL 2155).

Benzothiazole derivatives have been found to be useful in the treatment of various disorders, e.g. disorders of the autoimmune and neuronal systems as well as inflammatory disorders (WO 01/47920, WO 03/091249 and WO 03/047570). The oral administration route is preferred, especially for chronic indications.

SUMMARY OF THE INVENTION

The present invention is directed to macrogol glyceride pharmaceutical formulations containing benzothiazole derivatives. In particular, the invention relates to stearoyl macrogol glyceride formulations of benzothiazole derivatives, methods of preparation and use thereof.

According to an embodiment of the present invention, is provided a macrogol glyceride pharmaceutical formulation containing benzothiazole derivatives.

According to another embodiment of the invention, is provided a macrogol glyceride pharmaceutical formulation further comprising at least one poloxamer as excipient.

According to another embodiment of the invention, is provided a macrogol glyceride pharmaceutical formulation further comprising at least one poloxamer and one polyethylene glycol as excipient.

In a first aspect, the invention provides a macrogol glyceride pharmaceutical composition comprising a benzothiazole derivative according to Formula (I):

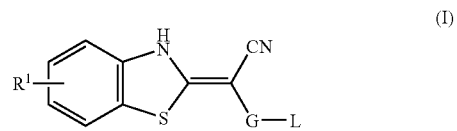

wherein $R^1$, G and L are defined in the detailed description.

In a second aspect, the invention provides a method for preparing a macrogol glyceride pharmaceutical composition comprising the steps of:
providing a benzothiazole derivative of Formula (I);
adding a benzothiazole according to Formula (I) to a molten preparation of macrogol glyceride.

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

DEFINITIONS

The term "macrogol glycerides" refers to saturated polyglycolized glycerides such as stearoyl-, lauroyl-, oleoly-, lineoyl-, caprylocaproyl-macrogol glycerides. Suitable macrogol glycerides according to the invention are Gelucires®.

The term "Gelucires®" refers to saturated polyglycolized glyceride which are a mixture of mono-, di- and triglycerides (fatty acid esters of glycerol) and mono- and di-fatty acid esters of polyethylene glycol (PEG or macrogol).

Examples of Gelucires® are Gelucire® 37/02, 37/06, 42/12, 44/14, 46/07, 48/09, 50/13, 53/10, 50/02, 54/02, 62/05 and 64/02, preferably 50/13.

The term "surfactant" refers to a soluble compound that reduces the surface tension of liquids, or reduces interfacial tension between two liquids or a liquid and a solid, the surface tension being the force acting on the surface of a liquid, tending to minimize the area of the surface. Surfactants have sometimes been used in pharmaceutical formulations, including delivery of low molecular mass drugs and polypeptides, in order to modify the absorption of the drug or its delivery to the target tissues. Well known surfactants include polysorbates (Polyoxyethylene derivatives; Tween) as well as poloxamers.

The term "Poloxamer" refers to a block copolymer of poly(ethylene oxide) and poly(propylene oxide), well-known as non-ionic surfactants, referred by the trade name Pluronics®. Examples of Poloxamers are Poloxamer 407 (Lutrol® F127 or Pluronic® F127), Poloxamer 338 (Lutrol® F108 or Pluronic® F108), Poloxamer 108 (Lutrol® F-38 or Pluronic® F-38) and Poloxamer 188 (Lutrol® F68 or Pluronic® F68), preferably Poloxamer 188 or Poloxamer 407.

The term "treatment" within the context of this invention refers to any beneficial effect on progression of disease, including attenuation, reduction, decrease or diminishing of the pathological development after the onset of the disease.

"$C_1$-$C_6$-alkyl" refers to alkyl groups having 1 to 6 carbon atoms. This term is exemplified by groups such as methyl, ethyl, n-propyl, isopropyl, n-butyl, isobutyl, tert-butyl, n-butyl, n-pentyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"Heterocycloalkyl" refers to a $C_3$-$C_8$-cycloalkyl group according to the definition above, in which 1 to 3 carbon atoms are replaced by hetero atoms chosen from the group consisting of O, S, NR, R being defined as hydrogen or $C_1$-$C_6$ alkyl. Preferred heterocycloalkyl include pyrrolidine, piperidine, piperazine, 1-methylpiperazine, morpholine, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_6$-alkyl groups having a carboxy substituent, including 2-carboxyethyl and the like.

"Acyl" refers to the group —C(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyl" refers to $C_1$-$C_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 membered cycloalkyl or heterocycloalkyl groups having an acyl substituent.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". "$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$- alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2-(propionylamino) ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", "alkoxy" and where R and R', together with the nitrogen atom to which they are attached, can optionally form a 3-8-membered hetero-cycloalkyl ring.

"$C_1$-$C_6$-alkyl amino" refers to $C_1$-$C_6$-alkyl groups having an amino substituent, including 2-(1-pyrrolidinyl)ethyl and the like.

"Ammonium" refers to a positively charged group —N+RR'R", where each R, R',R" is independently, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynyl heteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". "$C_1$-$C_6$-alkyl sulfonylamino" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminosulfonyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of: "$C_1$-$C_6$-alkyl", "$C_2$-$C_6$-alkenyl", "$C_2$-$C_6$-alkynyl", "cycloalkyl", "heterocycloalkyl", "aryl", "heteroaryl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively, said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of Formula (I) that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, methanesulfonic acid and poly-galacturonic acid. Said compounds can also be administered as pharmaceutically acceptable quaternary salts known by a person skilled in the art, which specifically include the quarternary ammonium salt of the formula —NR,R',R"$^+$Z$^-$, wherein R, R', R" is independently hydrogen, alkyl, or benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as Rebif® (Serono), Avonex® (Biogen) or Betaferon® (Schering).

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably, IFN-beta is intended to mean recombinant Interferon beta-1a.

IFN-β suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogs and active fragments thereof.

Rebif® (recombinant interferon-β) is the latest development in interferon therapy for multiple sclerosis (MS) and represents a significant advance in treatment. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

The dosing of IFN-β in the treatment of relapsing-remitting MS according to the invention depends on the type of IFN-β used.

In accordance with the present invention, where IFN is recombinant IFN-β1b produced in E. Coli, commercially available under the trademark Betaseron®, it may preferably be administered sub-cutaneously every second day at a dosage of about of 250 to 300 μg or 8 MIU to 9.6 MIU per person.

In accordance with the present invention, where IFN is recombinant IFN-β1a, produced in Chinese Hamster Ovary cells (CHO cells), commercially available under the trademark Avonex®, it may preferably be administered intramuscularly once a week at a dosage of about of 30 μg to 33 μg or 6 MIU to 6.6 MIU per person.

In accordance with the present invention, when IFN is recombinant IFN-β1a, produced in Chinese Hamster Ovary cells (CHO cells), commercially available under the trademark Rebif®, it may preferably be administered sub-cutaneously three times a week (TIW) at a dosage of 22 to 44 μg or 6 MIU to 12 MIU per person.

The Benzothiazoles

The benzothiazoles used in the invention are of Formula (I):

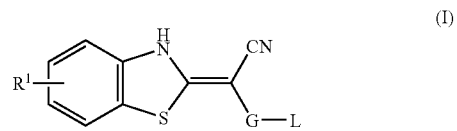

(I)

they comprise its tautomers, its geometrical isomers, its optically active forms as enantiomers, diastereomers and its racemate forms, as well as pharmaceutically acceptable salts thereof, wherein:

G is a pyrimidinyl group;

L is an optionally substituted alkoxy, or an amino group, or an optionally substituted 3-8 membered heterocycloalkyl, containing at least one heteroatom selected from N, O, S;

R$^1$ is selected from the group comprising or consisting of hydrogen, sulfonyl, amino, optionally substituted $C_1$-$C_6$-alkyl, optionally substituted $C_2$-$C_6$-alkenyl, optionally substituted $C_2$-$C_6$-alkynyl or optionally substituted alkoxy, aryl, halogen, cyano or hydroxy.

According to one embodiment, the benzothiazole tautomers are compounds of formulae (Ia), (Ia') or (Ia"):

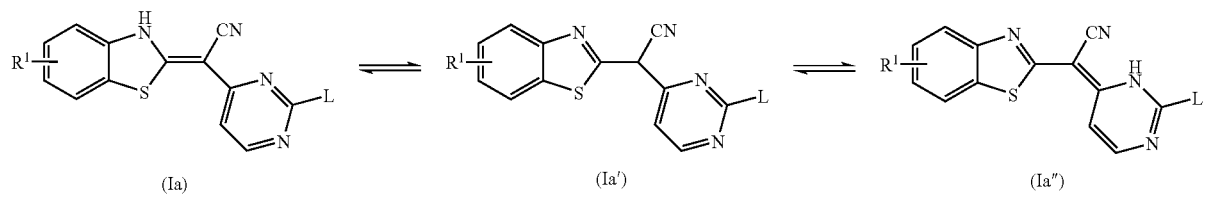

(Ia)   (Ia′)   (Ia″)

wherein $R^1$ is selected from the group comprising or consisting of hydrogen, sulfonyl, amino, optionally substituted $C_1$-$C_6$-alkyl, optionally substituted $C_2$-$C_6$-alkenyl, optionally substituted $C_2$-$C_6$-alkynyl or optionally substituted alkoxy, optionally substituted aryl, halogen, cyano or hydroxy;

L is an amino group of the formula —$NR^3R^4$ wherein $R^3$ and $R^4$ are each independently from each other H, optionally substituted $C_1$-$C_6$-alkyl, optionally substituted $C_2$-$C_6$-alkenyl, optionally substituted $C_2$-$C_6$-alkynyl, optionally substituted alkoxy, optionally substituted aryl, optionally substituted heteroaryl, optionally substituted saturated or unsaturated 3-8-membered cycloalkyl, optionally substituted 3-8-membered heterocycloalkyl, (wherein said cycloalkyl, heterocycloalkyl, optionally substituted aryl or optionally substituted heteroaryl groups may be fused with 1-2 further optionally substituted cycloalkyl, optionally substituted heterocycloalkyl, optionally substituted aryl or optionally substituted heteroaryl group), optionally substituted $C_1$-$C_6$-alkyl aryl, optionally substituted $C_1$-$C_6$-alkyl heteroaryl, optionally substituted $C_1$-$C_6$-alkenyl aryl, optionally substituted $C_1$-$C_6$-alkenyl heteroaryl, optionally substituted $C_1$-$C_6$-alkynyl aryl, optionally substituted $C_1$-$C_6$-alkynyl heteroaryl, optionally substituted $C_1$-$C_6$-alkyl cycloalkyl, optionally substituted $C_1$-$C_6$-alkyl heterocycloalkyl, optionally substituted $C_1$-$C_6$-alkenyl cycloalkyl, optionally substituted $C_1$-$C_6$-alkenyl heterocycloalkyl, optionally substituted $C_1$-$C_6$-alkynyl cycloalkyl, optionally substituted $C_1$-$C_6$-alkynyl heterocycloalkyl; or $R^3$ and $R^4$ may form a ring together with the nitrogen to which they are bound.

According to one embodiment, the L group in the benzothiazoles according to Formula (I) is selected from:

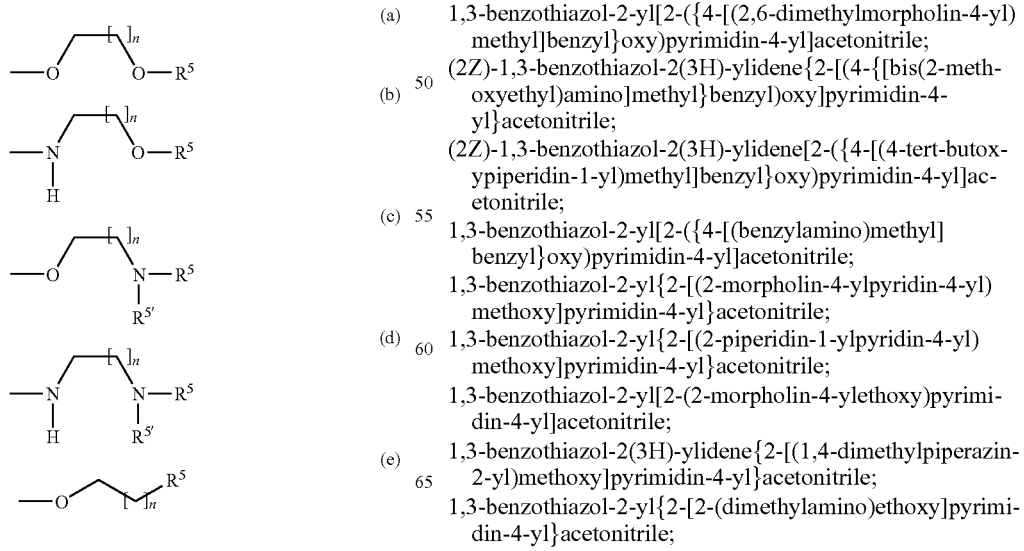

wherein n is 1 to 10, preferably selected from 1, 2, 3, 4, 5 and 6;

$R^5$ and $R^{5'}$ are independently selected from each other from the group consisting of H, substituted or unsubstituted $C_1$-$C_{10}$ alkyl, substituted or unsubstituted aryl or heteroaryl, substituted or unsubstituted heterocycloalkyl, substituted or unsubstituted, substituted or unsubstituted $C_1$-$C_6$ alkyl-aryl and substituted or unsubstituted $C_1$-$C_6$-alkyl-heteroaryl.

Specific benzothiazole acetonitriles according to Formula (I) include:

1,3 benzothiazol-2-yl-[2-(4-morpholin-4-ylmethyl-benzyloxy)-pyrimidin-4-yl]-acetonitrile;

1,3-benzothiazol-2-yl[2-(2-pyridin-3-ylethoxy)pyrimidin-4-yl]acetonitrile;

1,3-benzothiazol-2-yl[2-(quinolin-6-yloxy)pyrimidin-4-yl]acetonitrile;

1,3-benzothiazol-2-yl{2-[(5-morpholin-4-ylpyridin-3-yl)methoxy]pyrimidin-4-yl}acetonitrile;

1,3-benzothiazol-2-yl(2-{[4-(3,4-dihydroisoquinolin-2(1H)-ylmethyl)benzyl]oxy}pyrimidin-4-yl)acetonitrile;

1,3-benzothiazol-2-yl[2-(hexyloxy)pyrimidin-4-yl]acetonitrile;

1,3-benzothiazol-2-yl(2-{[3-(morpholin-4-ylmethyl)benzyl]oxy}pyrimidin-4-yl)acetonitrile;

1,3-benzothiazol-2-yl(2-{[3-(1H-imidazol-1-ylmethyl)benzyl]oxy}pyrimidin-4-yl)acetonitrile;

1,3-benzothiazol-2-yl(2-{[3-(piperidin-1-ylmethyl)benzyl]oxy}pyrimidin-4-yl)acetonitrile;

1,3-benzothiazol-2-yl[2-({4-[(2,6-dimethylmorpholin-4-yl)methyl]benzyl}oxy)pyrimidin-4-yl]acetonitrile;

(2Z)-1,3-benzothiazol-2(3H)-ylidene{2-[(4-{[bis(2-methoxyethyl)amino]methyl}benzyl)oxy]pyrimidin-4-yl}acetonitrile;

(2Z)-1,3-benzothiazol-2(3H)-ylidene[2-({4-[(4-tert-butoxypiperidin-1-yl)methyl]benzyl}oxy)pyrimidin-4-yl]acetonitrile;

1,3-benzothiazol-2-yl[2-({4-[(benzylamino)methyl]benzyl}oxy)pyrimidin-4-yl]acetonitrile;

1,3-benzothiazol-2-yl{2-[(2-morpholin-4-ylpyridin-4-yl)methoxy]pyrimidin-4-yl}acetonitrile;

1,3-benzothiazol-2-yl{2-[(2-piperidin-1-ylpyridin-4-yl)methoxy]pyrimidin-4-yl}acetonitrile;

1,3-benzothiazol-2-yl[2-(2-morpholin-4-ylethoxy)pyrimidin-4-yl]acetonitrile;

1,3-benzothiazol-2(3H)-ylidene{2-[(1,4-dimethylpiperazin-2-yl)methoxy]pyrimidin-4-yl}acetonitrile;

1,3-benzothiazol-2-yl{2-[2-(dimethylamino)ethoxy]pyrimidin-4-yl}acetonitrile;

1,3-benzothiazol-2(3H)-ylidene[2-({4-[(4-methylpiperazin-1-yl)carbonyl]benzyl}oxy)pyrimidin-4-yl]acetonitrile;

1,3-benzothiazol-2-yl{2-[3-(dimethylamino)propoxy]pyrimidin-4-yl}acetonitrile;

1,3-benzothiazol-2-yl(2-{2-[2-(dimethylamino)ethoxy]ethoxy}pyrimidin-4-yl)acetonitrile;

1,3-benzothiazol-2-yl{2-[2-(4-methylpiperazin-1-yl)ethoxy]pyrimidin-4-yl}acetonitrile.

According to another embodiment, the benzothiazoles according to Formula (I) include benzothiazoles of Formula (Ib):

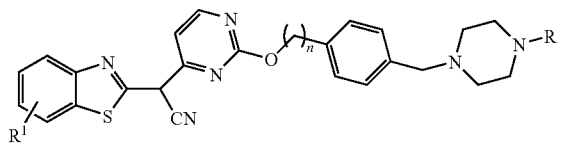

(Ib)

Wherein R in formula (Ib) is selected from the group comprising or consisting of hydrogen, substituted or unsubstituted $C_1$-$C_6$-alkyl, substituted or unsubstituted $C_1$-$C_6$-alkyl aryl, substituted or unsubstituted heteroaryl, substituted or unsubstituted $C_1$-$C_6$-alkyl heteroaryl, substituted or unsubstituted $C_2$-$C_6$-alkenyl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl, substituted or unsubstituted $C_2$-$C_6$-alkynyl aryl, substituted or unsubstituted $C_2$-$C_6$-alkynyl heteroaryl, substituted or unsubstituted $C_3$-$C_8$-cycloalkyl, substituted or unsubstituted heterocycloalkyl, substituted or unsubstituted $C_1$-$C_6$-alkyl cycloalkyl, substituted or unsubstituted $C_1$-$C_6$-alkyl heterocycloalkyl, substituted or unsubstituted $C_1$-$C_6$-alkyl carboxy, acyl, substituted or unsubstituted $C_1$-$C_6$-alkyl acyl, acyloxy, substituted or unsubstituted $C_1$-$C_6$-alkyl acyloxy, substituted or unsubstituted $C_1$-$C_6$-alkyl alkoxy, alkoxycarbonyl, substituted or unsubstituted $C_1$-$C_6$-alkyl alkoxycarbonyl, aminocarbonyl, substituted or unsubstituted $C_1$-$C_6$-alkyl aminocarbonyl, acylamino, substituted or unsubstituted $C_1$-$C_6$-alkyl acylamino, ureido, substituted or unsubstituted $C_1$-$C_6$-alkyl ureido, amino, substituted or unsubstituted $C_1$-$C_6$-alkyl amino, sulfonyloxy, substituted or unsubstituted $C_1$-$C_6$-alkyl sulfonyloxy, sulfonyl, substituted or unsubstituted $C_1$-$C_6$-alkyl sulfonyl, sulfinyl, substituted or unsubstituted $C_1$-$C_6$-alkyl sulfinyl, sulfanyl, substituted or unsubstituted $C_1$-$C_6$-alkyl sulfanyl, sulfonylamino, substituted or unsubstituted $C_1$-$C_6$-alkyl sulfonylamino;

$R^1$ is selected from the group comprising or consisting of H, halogen, cyano, nitro, amino, substituted or unsubstituted $C_1$-$C_6$-alkyl, in particular $C_1$-$C_3$ alkyl, like methyl or ethyl or —$CF_3$, substituted or unsubstituted $C_2$-$C_6$-alkenyl, substituted or unsubstituted $C_2$-$C_6$-alkynyl, substituted or unsubstituted $C_1$-$C_6$-alkyl-aryl, substituted or unsubstituted aryl or substituted or unsubstituted heteroaryl, substituted or unsubstituted $C_1$-$C_6$-alkyl-heteroaryl, —C(O)—$OR^2$, —C(O)—$R^2$, —C(O)—$NR^2R^{2'}$, —($SO_2$)$R^2$;

$R^2$ and $R^{2'}$ being independently selected from the group comprising or consisting of hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted aryl, unsubstituted or substituted heteroaryl, unsubstituted or substituted $C_1$-$C_6$-alkyl aryl, unsubstituted or substituted $C_1$-$C_6$-alkyl heteroaryl. Preferably $R^1$ is H; and n is an integer selected from 0, 1, 2 and 3, more preferred is 1 or 2.

The benzothiazoles used in the invention of Formula (Ib) also comprises the corresponding tautomers having the following Formula (Ib'):

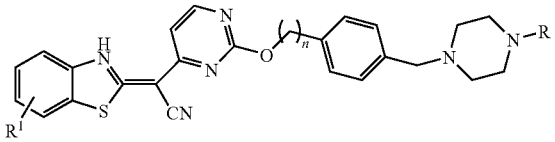

(Ib')

Specific examples of compounds of Formula (I) include the following:

1,3-benzothiazol-2-yl[2-({4-[(4-methylpiperazin-1-yl)methyl]benzyl}oxy)pyrimidin-4-yl]acetonitrile;

1,3-benzothiazol-2-yl-{2-[4-(4-benzyl-piperazin-1-ylmethyl)-benzyloxy]-pyrimidin-4-yl}-acetonitrile;

(3H-Benzothiazol-2-ylidene)-{2-[4-(4-ethyl-piperazin-1-ylmethyl)-benzyloxy]-pyrimidin-4-yl}-acetonitrile;

(3H-Benzothiazol-2-ylidene)-(2-{4-[4-(2-methoxy-ethyl)-piperazin-1-ylmethyl]-benzyloxy}-pyrimidin-4-yl)-acetonitrile;

1,3-benzothiazol-2-yl[2-({4-[(4-benzyl-piperazin-1-yl)methyl]-benzyl}oxy)pyrimidin-4-yl]acetonitrile;

1,3-benzothiazol-2-yl[2-({4-[(4-formylpiperazin-1-yl)methyl]benzyl}oxy)pyrimidin-4-yl]acetonitrile;

(2-{4-[4-(2-Amino-acetyl)-piperazin-1-ylmethyl]-benzyloxy}-pyrimidin-4-yl)-(3H-benzothiazol-2-ylidene)-acetonitrile;

[2-({4-[(4-acetylpiperazin-1-yl)methyl]benzyl}oxy)pyrimidin-4-yl](1,3-benzothiazol-2-yl)acetonitrile;

4-(4-{4-[(3H-Benzothiazol-2-ylidene)-cyano-methyl]-pyrimidin-2-yloxymethyl}-benzyl)-piperazine-1-carboxylic acid dimethylamide;

4-(4-{4-[(3H-Benzothiazol-2-ylidene)-cyano-methyl]-pyrimidin-2-yloxymethyl}-benzyl)-piperazine-1-carboxylic acid methyl ester;

(3H-Benzothiazol-2-ylidene)-{2-[4-(4-[1,2,4]oxadiazol-3-ylmethyl-piperazin-1-yl methyl)-benzyloxy]-pyrimidin-4-yl}-acetonitrile;

(3H-Benzothiazol-2-ylidene)-(2-{4-[4-(2-hydroxy-ethyl)-piperazin-1-ylmethyl]-benzyloxy}-pyrimidin-4-yl)-acetonitrile;

[4-(4-{4-[(3H-Benzothiazol-2-ylidene)-cyano-methyl]-pyrimidin-2-yloxymethyl}-benzyl)-piperazin-1-yl]-acetic acid methyl ester;

2-[4-(4-{4-[(3H-Benzothiazol-2-ylidene)-cyano-methyl]-pyrimidin-2-yloxymethyl}-benzyl)-piperazin-1-yl]-acetamide;

1,3-benzothiazol-2-yl[2-({3-[(4-methylpiperazin-1-yl)methyl]benzyl}oxy)pyrimidin-4-yl]acetonitrile.

The benzothiazoles according to Formula (I) are synthesized according to methods as described in WO 01/47920, preferably according to methods described in WO 03/091249.

The benzothiazoles according to Formula (I) can be synthesized according to methods described in Schemes I to VIII below.

Scheme I

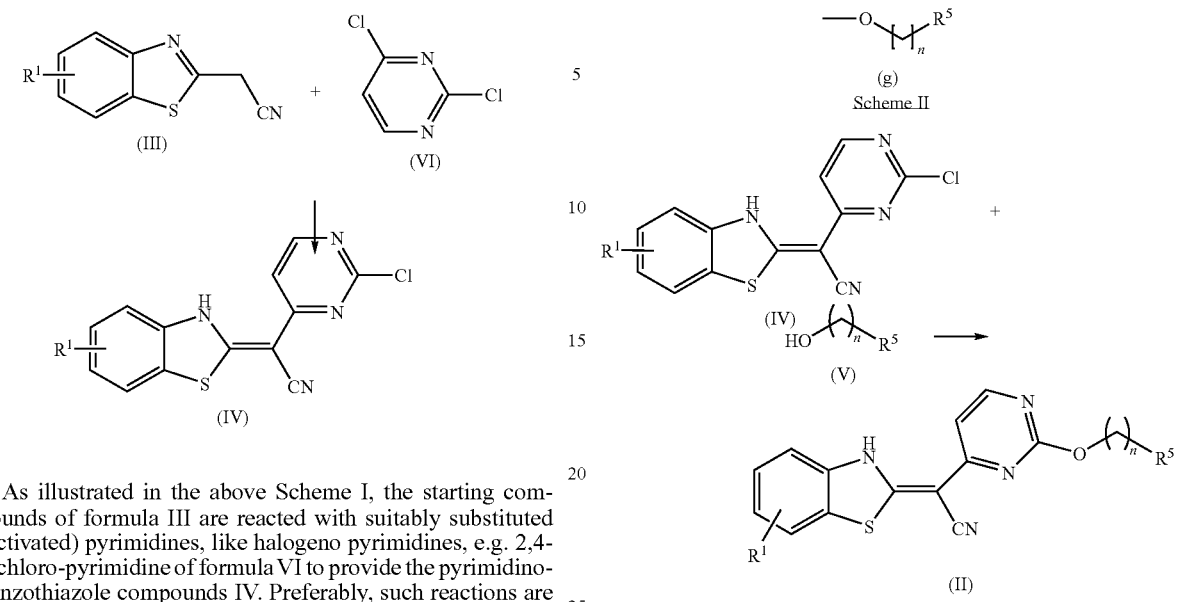

As illustrated in the above Scheme I, the starting compounds of formula III are reacted with suitably substituted (activated) pyrimidines, like halogeno pyrimidines, e.g. 2,4-dichloro-pyrimidine of formula VI to provide the pyrimidinobenzothiazole compounds IV. Preferably, such reactions are performed in the presence of suitable bases, e.g. sodium hydride, potassium hydride and the like in an anhydrous inert atmosphere, preferably in a polar solvent like DMF, DMA, MeCN or THF at a temperature in the range of about −78° C. to 100° C. (Chabaka et al., *Pol. J. Chem.* 1994, 1317-1326). Benzothiazoles of formula III are either commercially available, such as from Maybridge Chemical Co. Ltd or can be prepared from commercially available compounds by conventional procedures.

Halogenated pyrimidines, e.g. 2,4-dichloropyrimidine of formula VI, are also either commercially available, such as from Aldrich, Fluka, Sigma and the like or may be prepared by conventional procedures.

For obtaining the final benzothiazoles of formula (II), i.e. benzothiazoles of formula Ia wherein L is of formula (g) below, and wherein n and $R^5$ are as defined above, the intermediate compounds of formula (IV) are preferably reacted with suitable alcohols of formula (V), as illustrated in Scheme II below.

The reaction is preferably performed in the presence of solvents such as DMF, DMA, NMP, DMSO or ACN, most preferably in DMA or MeCN, in the presence of a suitable base such as tBuOK, $CS_2CO_3$ with or without CuI, NaH, or the like, most preferably NaH, at a temperature in the range of about 25 to 120° C. In a preferred method, the starting compounds are heated at 25° up to 100° C. in solution in MeCN in the presence of NaH.

The intermediate compounds of formula (V) may be obtained through commercial sources or by a synthetic approach which is illustrated in Scheme III to VII.

In said Schemes III and IV, the starting building block is methyl-p-toluate (Scheme III) or its meta analogue (Scheme IV) to prepare the corresponding benzyl alcohol intermediates, in a 4 step process, including the formation of the ester, the bromination of the methyl group, alkylation with the corresponding amine and the reduction of the ester to access the final substituted benzyl alcohols.

Scheme III

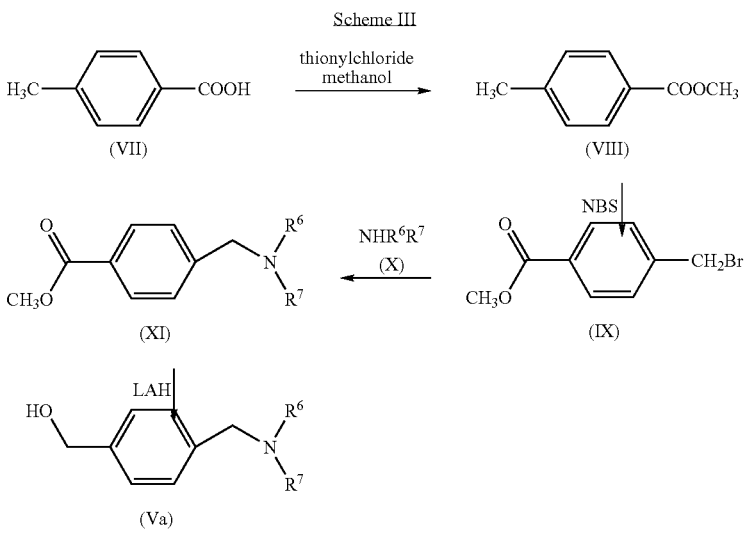

Wherein $R^6$ and $R^7$ are independently selected from $R^5$ and $R^{5'}$ or $R^6$ and $R^7$ can form a ring selected from together with the nitrogen they are attached to form a substituted or unsubstituted heteroaryl or a substituted or unsubstituted heterocycle.

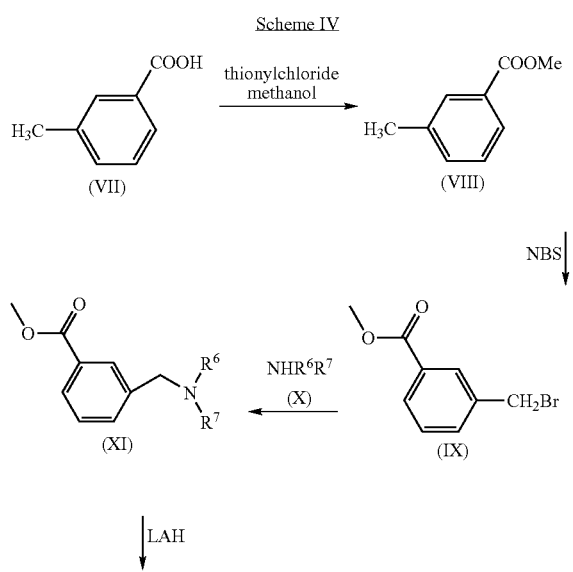

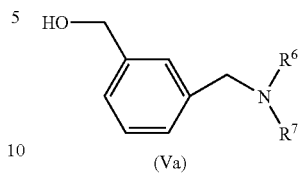

In said Scheme V below, the starting building block is 2-amino-4-methyl-pyridine to prepare the corresponding 4-hydroxymethyl pyridine intermediates, in a 5 step process, including a the transformation of the 2-amino group in a 2-bromo, an oxidation, an alkylation with the corresponding amine, the formation of the methyl ester and the reduction of the ester to access the final substituted 4-hydroxymethyl pyridines.

In said Scheme VI below, the starting building block is 5-bromo-nicotinic acid methyl ester to prepare the corresponding 2-hydroxymethyl pyridine intermediates, in a 2 step process, including an alkylation with the corresponding amine, the formation of the methyl ester and the reduction of the ester to access the final substituted 2-hydroxymethyl pyridines.

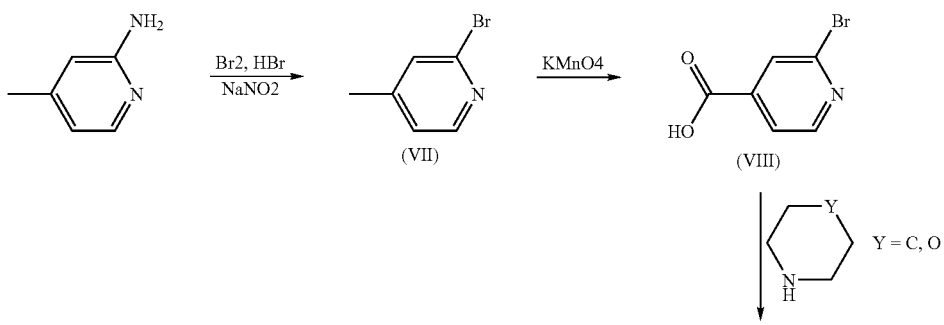

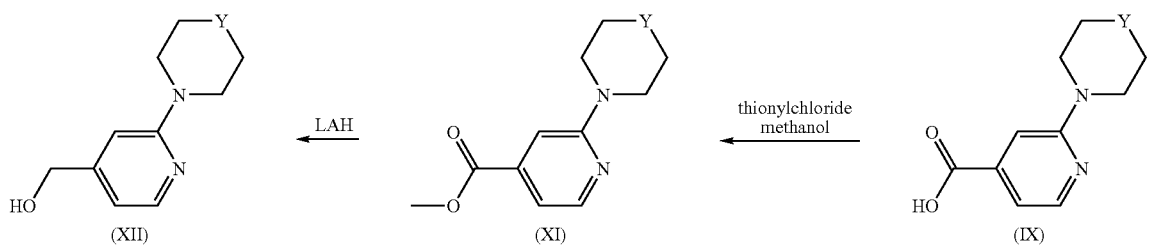

Scheme VI

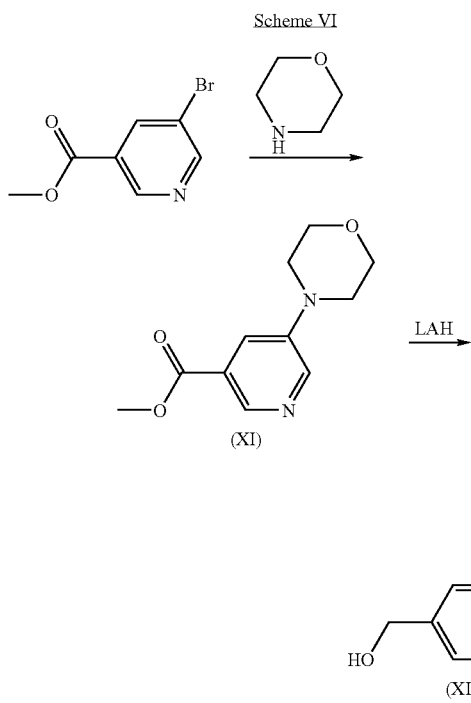

In said Scheme VII below, the starting material is 1-(2-hydroxyethyl)-piperazine to prepare the corresponding alcohol intermediate by reductive alkylation.

Scheme VII

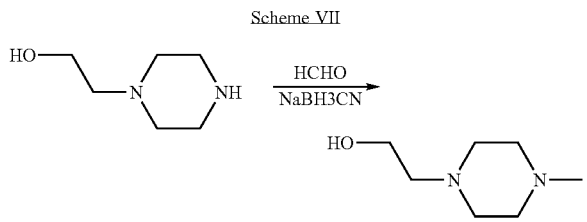

In said Scheme VIII below, the starting material is 4-(hydroxymethyl)benzoic methyl ester to prepare the corresponding benzyl alcohol intermediates, by coupling of the amine in the presence of trimethyl aluminium.

Scheme VIII

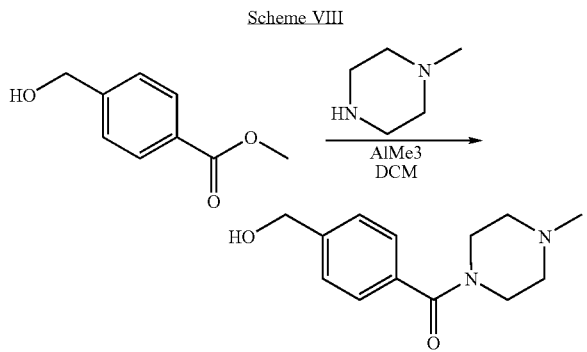

Excipients

According to one embodiment of the invention, poloxamers (Pluronics) are surfactants that are preferably used in macrogol glyceride formulations of the invention.

Examples of poloxamers are Pluronic® F77 (Poloxamer 217), Pluronic® F87 (Poloxamer 237), Pluronic® F88 (Poloxamer 238) and Pluronic® F68 (Poloxamer 188), particularly preferably Pluronic® F68.

According to one embodiment of the invention, polyethylene glycol are excipient that are preferably used in macrogol glyceride formulations of the invention, preferably polymer of polyethylene oxide such as PEG-2000, PEG-4000, PEG-6000, PEG-10 000, PEG-20 000, preferably PEG-6000.

Macrogol Glyceride Formulations of the Invention

According to one embodiment, the invention provides a pharmaceutical composition comprising a benzothiazole of Formula (I):

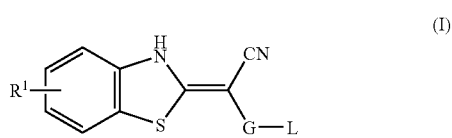

as well as its tautomers, its geometrical isomers, its optically active forms as enantiomers, diastereomers and its racemate forms, as well as pharmaceutically acceptable salts thereof, wherein G, L and $R^1$ are as defined above; and a macrogol glyceride.

In a further embodiment, the invention provides a pharmaceutical composition according to the invention wherein the macrogol glyceride is a stearoyl glyceride.

In another further embodiment, the invention provides a pharmaceutical composition according to the invention wherein the macrogol glyceride is Gelucire® 50/13.

In another further embodiment, the invention provides a pharmaceutical composition according to the invention wherein the composition comprises Gelucire® 50/13 in an amount of 40 to 95% w/w relative to the total composition, preferably 40 to 80% w/w relative to the total composition, including 40, 50, 60, 70 and 80% w/w.

In another further embodiment, the invention provides a pharmaceutical composition according to the invention wherein the composition comprises Gelucire® 50/13 in an amount of 40 to 60% w/w relative to the total composition.

In another embodiment, the invention provides a pharmaceutical composition according to the invention containing an amount of benzothiazole of 5% w/w to 40% w/w relative to the total composition, preferably of 20% to 40% w/w relative to the total composition, including 20, 30 and 40% w/w.

In another embodiment, the invention provides a pharmaceutical composition according to the invention wherein the benzothiazole is 1,3 benzothiazol-2-yl-[2-(4-morpholin-4-ylmethyl-benzyloxy)-pyrimidin-4-yl]-acetonitrile.

In another embodiment, the invention provides a pharmaceutical composition according to the invention wherein the benzothiazole is 1,3 benzothiazol-2-yl-[2-(4-morpholin-4-ylmethyl-benzyloxy)-pyrimidin-4-yl]-acetonitrile, mesylate salt.

In another embodiment, the invention provides a pharmaceutical composition according to the invention wherein the benzothiazole is in a non-crystalline, i.e. the crystallinity of the benzothiazole is less than 50%, preferably less than about 40 to 10%, more preferably less than or about 5%.

In another embodiment, the invention provides a pharmaceutical composition according to the invention wherein the composition further comprises a poloxamer.

In another embodiment, the invention provides a pharmaceutical composition according to the invention wherein the composition further comprises a poloxamer and wherein the poloxamer is Poloxamer 188.

In another embodiment, the invention provides a pharmaceutical composition according to the invention wherein the composition further comprises a Polyethylene Glycol (PEG).

In a further embodiment, the invention provides a pharmaceutical composition according to the invention wherein the composition further comprises a Polyethylene Glycol (PEG) and wherein the Polyethylene Glycol is PEG-6 000.

In another embodiment, the invention provides a pharmaceutical composition according comprises at least 20% w/w 1,3 benzothiazol-2-yl-[2-(4-morpholin-4-ylmethyl-benzyloxy)-pyrimidin-4-yl]-acetonitrile, mesylate salt and Gelucire® 50/13 in an amount of 40 to 80% w/w relative to the total composition.

In another embodiment, the invention provides a pharmaceutical composition selected from the group:

| | |
|---|---|
| 1,3benzothiazol-2-yl-[2-(4-morpholin-4-ylmethyl-benzyloxy)-pyrimidin-4-yl]-acetonitrile, mesylate salt | 20% w/w |
| Gelucire ® 50/13 | 80% w/w; |
| 1,3benzothiazol-2-yl-[2-(4-morpholin-4-ylmethyl-benzyloxy)-pyrimidin-4-yl]-acetonitrile, mesylate salt | 30% w/w |
| Gelucire ® 50/13 | 70% w/w; |
| 1,3benzothiazol-2-yl-[2-(4-morpholin-4-ylmethyl-benzyloxy)-pyrimidin-4-yl]-acetonitrile, mesylate salt | 40% w/w |
| Gelucire ® 50/13 | 60% w/w; |
| 1,3 benzothiazol-2-yl-[2-(4-morpholin-4-ylmethyl-benzyloxy)-pyrimidin-4-yl]-acetonitrile, mesylate salt | 20% w/w |
| Gelucire ® 50/13 | 40% w/w |
| Lutrol ® F68 | 40% w/w; |
| 1,3 benzothiazol-2-yl-[2-(4-morpholin-4-ylmethyl-benzyloxy)-pyrimidin-4-yl]-acetonitrile,, mesylate salt | 20% w/w |
| Gelucire ® 50/13 | 40% w/w |
| Lutrol ® E6000 | 40% w/w; |
| And | |
| 1,3 benzothiazol-2-yl-[2-(4-morpholin-4-ylmethyl-benzyloxy)-pyrimidin-4-yl]-acetonitrile, mesylate salt | 5% w/w |
| Gelucire ® 50/13 | 95% w/w. |

The formulations of the invention both increase the dissolution rate and the bioavailability of benzothiazoles of the invention.

In another embodiment, the invention provides a method for preparing a composition according to the invention wherein said method comprises the steps of:
  providing a benzothiazole according to Formula (I)
  adding a calculated amount of a benzothiazole according to Formula (I) to a molten preparation of macrogol glyceride.

Typically, a macrogol glyceride preparation is heated under a suitable temperature under stirring in order to obtain a molten preparation of macrogol glyceride for use in the method according to the invention. For example, macrogol glyceride preparations of Gelucire® 50/13 can be melted by heating up to about 60-80° C. such as to about 60-70° C., during about 30 min to 1 hour, especially about 30 to 40 minutes under stirring.

In a further embodiment, the invention provides a method for preparing a composition wherein the benzothiazole is incorporated in a powder form into the macrogol glyceride molten preparation under stirring.

In a further embodiment, the invention provides a method for preparing a composition wherein the benzothiazole is incorporated in a powder form into the macrogol glyceride molten preparation under stirring and wherein the method further comprises the steps of:
  cooling down the homogenous molten dispersion
  grinding the obtained solid into particles.

Typically, the cooling step is performed in order to obtain a rapid cooling of the preparation, for example in an ice bath or by pouring the melted preparation into liquid nitrogen. Typically, the cooling in an ice bath can be carried out for about 1 hour to 3 hours.

The grinding step leads to coarse or fine particles (powder) depending on the different types of milling equipment used. Typically, a milling equipment that can be used in the context of the invention is a hammer and/or blades mill, such as for example FitzMill®.

In another further embodiment, the invention provides a method for preparing a composition wherein the benzothiazole is incorporated in a powder form into the macrogol glyceride molten preparation under stirring and wherein the method further comprises the step of cooling down the homogenous molten dispersion by spray chilling or spray congealing.

Typically, the benzothiazole-loaded Gelucire formulation is stirred or hamogenised before being transferred to the reactor. The excipient/suspension is typically maintained in the reactor under stirring at a temperature between 50° C. and 80° C.

The benzothiazole-loaded Gelucire is transferred from the reactor to the cooling chamber by pressurizing the vessel (e.g. at 100 mbar or more) through feeding pipes that are maintained at a temperature sufficient to avoid the cooling of the suspension inside the pipes.

The benzothiazole-loaded Gelucire is introduced in the cooling chamber through a nozzle under nitrogen flux (atomizing nitrogen) at a high enough temperature, for example between 50-80° C.

Cold nitrogen gas (nitrogen for congealing) is flushed into the cooling chamber, typically at a temperature between −50° C. and +20° C., but preferably at a temperature between −30° C. and +10° C.

The temperature of the nozzle is preferably held above 50° C. to avoid any blockage. The distance between reactor and nozzle is minimized to reduce pressure drop in the feed line.

Size of the nozzles is adjusted depending on the viscosity of the suspension, e.g. larger nozzles (orifice 1.4 mm/cap 2.2 mm) are preferably used for suspension with higher viscosity.

The so-obtained particles or pellets are collected then collected in the collection chamber.

The spray chilling method has the advantage to achieve good yields (typically of about 55% or higher), to provide particles with regular shapes and sizes that exhibit improved solubility profiles compared to bulk. This process has therefore the further advantage to allow to skip the step of grinding the particles.

In another further embodiment, the invention provides a method for preparing a composition wherein the benzothiazole is incorporated in a water solution form (i.e. dissolved) into the macrogol glyceride molten preparation under stirring. Typically, the benzothiazole is dissolved in water and then added into the macrogol glyceride molten preparation under stirring to form an emulsion (Oil/Water or Water/Oil). In particular, the method further comprises an atomisation step wherein the formed emulsion is sprayed through a nebulizer or a capillary nozzle in presence of liquid $CO_2$. An example of atomisation method that can be used in the atomisation step above is the one described in WO 2005/049192.

In another further embodiment, the method for preparing a composition according to the invention wherein the benzothiazole is incorporated in a water solution form, optionally further comprises a freeze-drying step after the atomisation step.

Typical, stirring methods that can be use in the context of the invention are vortex stirring methods.

In a further embodiment, the invention provides a use of a benzothiazole macrogol glyceride formulation according to the invention for the preparation of a pharmaceutical composition for the treatment of disorders selected from autoimmune disorders, such as multiple sclerosis and rheumatoid arthritis, respiratory disorders such as asthma, neurodegenerative or neuronal system disorders, such as Alzheimer's disease, Parkinson's disease, epilepsy and seizures, Huntington's disease, CNS disorders, traumatic brain injuries as well as ischemic disorders and hemorrhaging strokes, inflammatory disorders, scleroderma and scleroderma-like disorders, cancer, endometriosis, fibrosis, such as lung fibrosis and diabetes.

In a further embodiment, the invention provides a method for the treatment of disorders selected from autoimmune disorders, such as multiple sclerosis and rheumatoid arthritis, respiratory disorders such as asthma, neurodegenerative or neuronal system disorders, inflammatory disorders, cancer, endometriosis, fibrosis, such as lung fibrosis and diabetes comprising the administration of benzothiazole macrogol glyceride formulation according to the invention to a patient in need thereof.

The formulations described herein, may be useful for the treatment of a disease, especially a disease selected from autoimmune disorders, such as multiple sclerosis and rheumatoid arthritis, respiratory disorders such as asthma, neurodegenerative or neuronal system disorders, such as Alzheimer's disease, Parkinson's disease, epilepsy and seizures, Huntington's disease, CNS disorders, traumatic brain injuries as well as ischemic disorders and hemorrhaging strokes, inflammatory disorders, scleroderma and scleroderma-like disorders, cancer, endometriosis, fibrosis, such as lung fibrosis and diabetes.

In another further embodiment, the invention provides Gelucire formulations of benzothiazoles according to the invention with improved solubility and/or bioavailibility compared to the bulk.

The benzothiazole in formulations described herein, may be administered to a patient in accordance with the present invention via a variety of delivery methods including oral administration, trans-mucosal, or other means appreciated by the skilled artisan, as well-known in the art.

The dosage administered to an individual will vary depending upon a variety of factors, including pharmacokinetic properties, the route of administration, patient conditions and characteristics (sex, age, body weight, health and size), extent of symptoms, concurrent treatments, frequency of treatment and the effect desired.

Standard dosages of benzothiazole in macrogol glyceride formulations according to the invention is 1 to 3 000 mg, preferably 10 to 1 000 mg.

Benzothiazole formulations according to the invention may be administered by oral route, in powder form and optionally as extemporaneous suspension of the powder in aqueous medium.

The formulations of the present invention may be provided in a solid unit dose form (dispersible powder or pellets in capsules, sachets, tablets) or as a powder or granules dispersible in water before administration as aqueous suspension.

All excipients commonly used in solid formulations as for example dispersing agents, surfactants, fillers, lubricants, binders, desintegrants, etc., and known to the skilled in the art can be used in the formulations of the present inventions. All excipients commonly used in aqueous suspensions formulations as for example dispersing agents, surfactants, viscosizing agents, wetting agents, suspending agents etc., and known to the skilled in the art can be used in the formulations of the present invention.

In another aspect, the invention provides the following novel compounds:

1,3-benzothiazol-2-yl[2-(2-pyridin-3-ylethoxy)pyrimidin-4-yl]acetonitrile;
1,3-benzothiazol-2-yl[2-(quinolin-6-yloxy)pyrimidin-4-yl] acetonitrile;
1,3-benzothiazol-2-yl{2-[(5-morpholin-4-ylpyridin-3-yl) methoxy]pyrimidin-4-yl}acetonitrile;
1,3-benzothiazol-2-yl[2-({3-[(4-methylpiperazin-1-yl)methyl]benzyl}oxy)pyrimidin-4-yl]acetonitrile;
1,3-benzothiazol-2-yl(2-{[4-(3,4-dihydroisoquinolin-2 (1H)-ylmethyl)benzyl]oxy}pyrimidin-4-yl) acetonitrile;
1,3-benzothiazol-2-yl[2-(hexyloxy)pyrimidin-4-yl]acetonitrile;
1,3-benzothiazol-2-yl(2-{[3-(morpholin-4-ylmethyl)benzyl] oxy}pyrimidin-4-yl)acetonitrile;
1,3-benzothiazol-2-yl(2-{[3-(1H-imidazol-1-ylmethyl)benzyl]oxy}pyrimidin-4-yl)acetonitrile;
1,3-benzothiazol-2-yl(2-{[3-(piperidin-1-ylmethyl)benzyl] oxy}pyrimidin-4-yl)acetonitrile;
1,3-benzothiazol-2-yl[2-({4-[(2,6-dimethylmorpholin-4-yl) methyl]benzyl}oxy)pyrimidin-4-yl]acetonitrile;
(2Z)-1,3-benzothiazol-2(3H)-ylidene {2-[(4-{[bis(2-methoxyethyl)amino]methyl}benzyl)oxy]pyrimidin-4-yl}acetonitrile;
(2Z)-1,3-benzothiazol-2(3H)-ylidene[2-({4-[(4-tert-butoxypiperidin-1-yl)methyl]benzyl}oxy)pyrimidin-4-yl]acetonitrile;
1,3-benzothiazol-2-yl[2-({4-[(benzylamino)methyl] benzyl}oxy)pyrimidin-4-yl]acetonitrile;
1,3-benzothiazol-2-yl{2-[(2-morpholin-4-ylpyridin-4-yl) methoxy]pyrimidin-4-yl}acetonitrile;
1,3-benzothiazol-2-yl{2-[(2-piperidin-1-ylpyridin-4-yl) methoxy]pyrimidin-4-yl}acetonitrile;
1,3-benzothiazol-2-yl[2-(2-morpholin-4-ylethoxy)pyrimidin-4-yl]acetonitrile;
1,3-benzothiazol-2(3H)-ylidene{2-[(1,4-dimethylpiperazin-2-yl)methoxy]pyrimidin-4-yl}acetonitrile;
1,3-benzothiazol-2-yl{2-[2-(dimethylamino)ethoxy]pyrimidin-4-yl}acetonitrile;
1,3-benzothiazol-2(3H)-ylidene[2-({4-[(4-methylpiperazin-1-yl)carbonyl]benzyl}oxy)pyrimidin-4-yl]acetonitrile;
1,3-benzothiazol-2-yl{2-[3-(dimethylamino)propoxy]pyrimidin-4-yl}acetonitrile;
1,3-benzothiazol-2-yl(2-{2-[2-(dimethylamino)ethoxy] ethoxy}pyrimidin-4-yl)acetonitrile;
1,3-benzothiazol-2-yl{2-[2-(4-methylpiperazin-1-yl) ethoxy]pyrimidin-4-yl}acetonitrile.

Another aspect of the invention, includes these compounds for use as medicaments.

Another aspect of the invention, includes the use of the compounds described herein for the preparation of a pharmaceutical formulation for the treatment of auto-immune disorders, including multiple sclerosis, inflammatory disorders, including rheumatoid arthritis, diabetes, fibrosis such as lung fibrosis, respiratory disorders such as asthma, cancer, neurodegenerative or neuronal system disorder such as Alzheimer's disease, Parkinson's disease, epilepsy and seizures, Huntington's disease, CNS disorders, traumatic brain injuries as well as ischemic disorders and hemorrhaging strokes, scleroderma-like disorders, cancer, endometriosis, fibrosis, such as lung fibrosis and diabetes.

The compound of the invention are useful for the treatment of auto-immune disorders, including multiple sclerosis, inflammatory disorders, including rheumatoid arthritis, diabetes, fibrosis such as lung fibrosis, respiratory disorders such as asthma, cancer, neurodegenerative or neuronal system disorder such as Alzheimer's disease, Parkinson's disease, epilepsy and seizures, Huntington's disease, CNS disorders, traumatic brain injuries as well as ischemic disorders and hemorrhaging strokes, scleroderma-like disorders, cancer, endometriosis, fibrosis, such as lung fibrosis and diabetes.

In another embodiment, the compounds and/or the formulations of the invention can be used in the treatment of autoimmune diseases, especially demyelinating diseases such as multiple sclerosis, alone or in combination with a co-agent useful in the treatment of autoimmune diseases, wherein the co-agent is for example selected from the following compounds:

(a) Interferons, e. g. pegylated or non-pegylated interferons, e. g. administered by sub-cutaneous, intramuscular or oral routes, preferably interferon beta;
(b) Glatiramer, e. g. in the acetate form;
(c) Immunosuppressants with optionally antiproliferative/antineoplastic activity, e. g. mitoxantrone, methotrexate, azathioprine, cyclophosphamide, or steroids, e. g. methylprednisolone, prednisone or dexamethasone, or steroid-secreting agents, e. g. ACTH;
(d) Adenosine deaminase inhibitors, e. g. Cladribine;
(e) Inhibitors of VCAM-1 expression or antagonists of its ligand, e. g. antagonists of the α4/β1 integrin VLA-4 and/or alpha-4-beta-7 integrins, e. g. natalizumab (ANTEGREN).

Further co-agents such as anti-inflammatory agents (in particular for demyelinating diseases such as multiple sclerosis) are described below:

A further anti-inflammatory agent is Teriflunomide which is described in WO 02/080897.

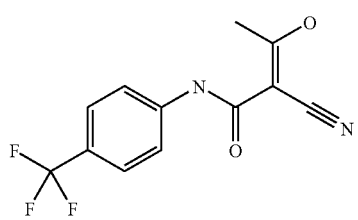

Still a further anti-inflammatory agent is Fingolimod which is described in EP 727406, WO 2004/028251 and WO 2004/028251.

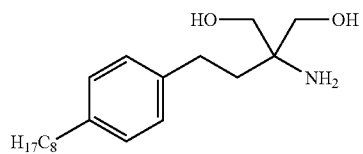

Still a further anti-inflammatory agent is Laquinimod which is described in WO 99/55678.

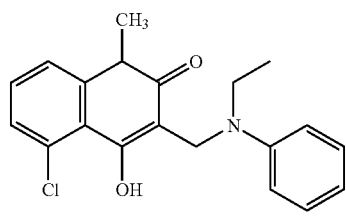

Still a further anti-inflammatory agent is Tensirolimus which is described in WO 02/28866.

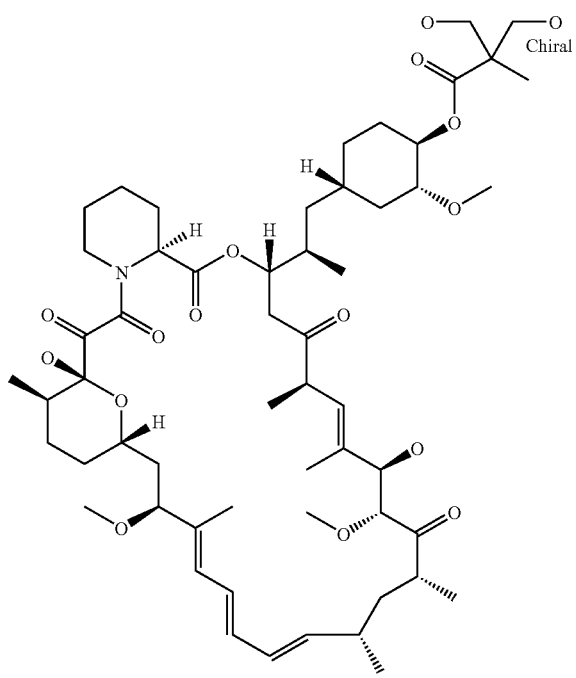

Still a further anti-inflammatory agent is Xaliprodene which is described in WO 98/48802.

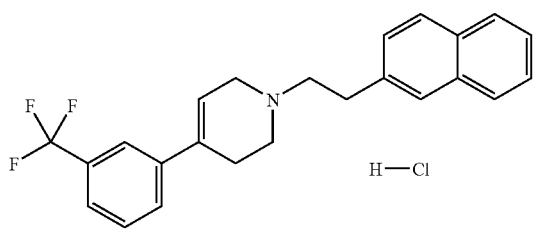

Still a further anti-inflammatory agent is Deskar Pirfenidone which is described in WO 03/068230.

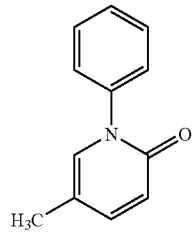

Still a further anti-inflammatory agent is the below benzothiazole derivative which is described in WO 01/47920.

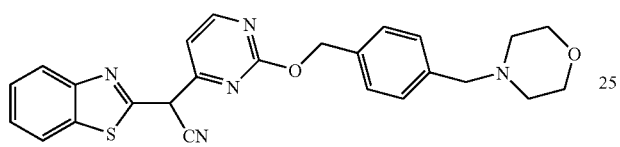

Still a further anti-inflammatory agent is the below hydroxamic acid derivative which is described in WO 03/070711.

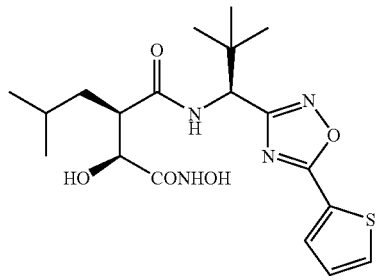

Still a further anti-inflammatory agent is MLN3897 which is described in WO 2004/043965.

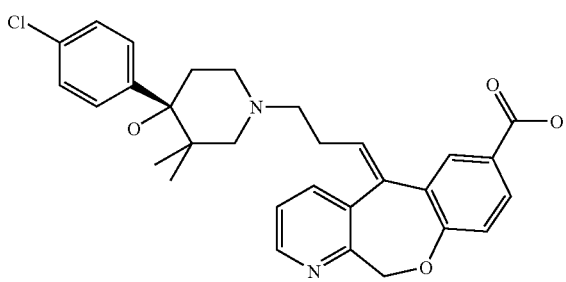

Still a further anti-inflammatory agent is CDP323 which is described in WO 99/67230.

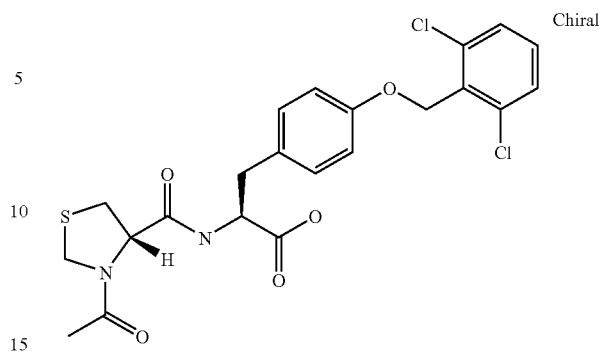

Still a further anti-inflammatory agent is Simvastatin which is described in WO 01/45698.

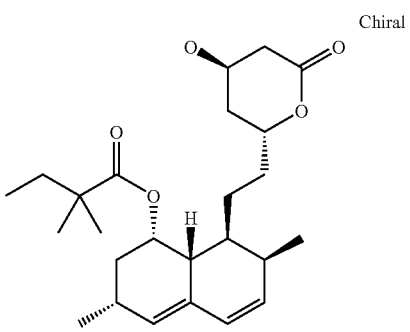

Still a further anti-inflammatory agent is Fampridine which is described in U.S. Pat. No. 5,540,938.

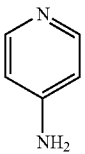

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning of a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skilled in the art.

The invention will now be described by means of the following Examples, which should not be construed as in any way limiting the present invention. The Examples will refer to the Figure specified here below.

EXAMPLES

Figure 1:
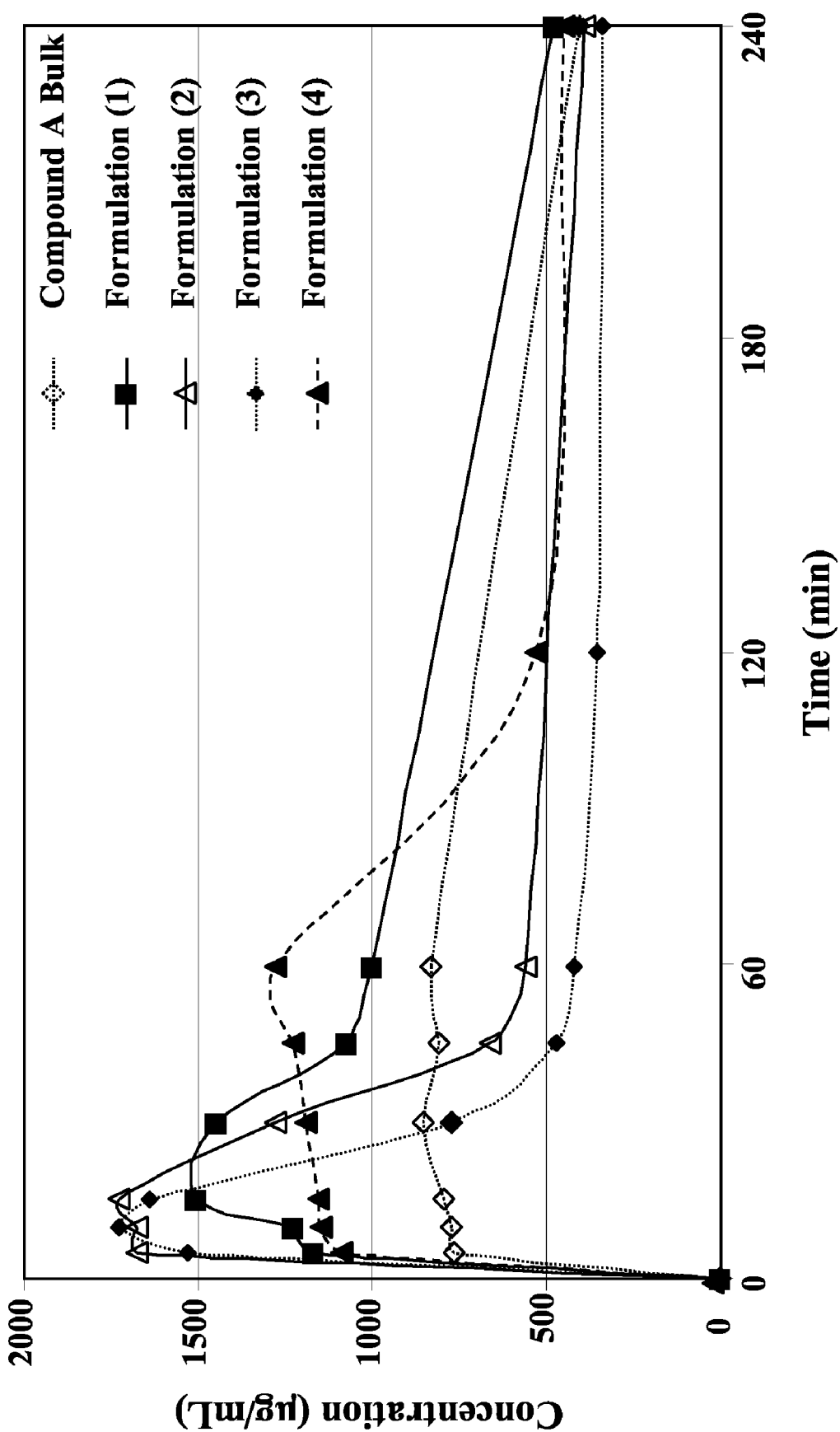
FIG. 1 shows the solubilization profile (expressed as concentration (μg/mL) versus time (min)) in oversaturation conditions, Fed State Simulated Intestinal Fluid (FeSSIF), pH=5 as dissolution medium) of Compound A in different solid powder (particles) formulations compared to bulk powder. Open lozenges: Compound A, solid bulk; Filled squares: Compound A, macrogol glyceride solid powder formulation (1); Open triangles: Compound A, macrogol glyceride solid formulation (2); Filled lozenges: Compound A, macrogol glyceride solid formulation (3); Filled triangles: Compound A, macrogol glyceride solid formulation (4).

The following abbreviations refer respectively to the definitions below:

Cm (centimeter), h (hour), kg (kilogram), mg (milligram), μg (microgram), μm (micrometer), min (minute), mm (millimeter), mmol (millimole), mM (millimolar), mL (milliliter), μL (microliter), ACN (acetonitrile), AUC (Area under the curve), Da (Dalton), DMF (dimethylformamide), DMSO (Dimethyl Sulfoxide), DSC (Differential Scanning calorimetry), FeSSIF (Fed State Simulated Intestinal Fluid), HLB (Hydrophilic Lipophilic Balance), HPLC (High Performance Liquid Chromatography), MS (mass spectrometry), MW (molecular weight), NMP (N-Methyl-2-Pyrrolidone), PBS (Phosphate Buffered Saline), RP-HPLC (Reverse Phase High Performance Liquid Chromatography), rpm (rotation per minute), THF (tetrahydrofuran).

Macrogol glycerides (Gelucires®) are commercially available, for example from Gattefossé.

Example 1

Benzothiazole Macrogol Glyceride Formulation (1)

1. General Preparation Procedure

A suitable amount of Gelucire® in powder form was melted in a thermostated water bath. A suitable amount of benzothiazole in powder form (20% w/w calculated on the total composition) was dispersed into the molten excipient. The mass was kept under stirring for about 30 min, until a homogeneous dispersion was obtained. The drug-loaded Gelucire® was then cooled down in an ice bath, and the solid mass was mechanically reduced (grinded) to a coarse powder. The so-obtained particles were micronized with a hammer and/or blades mill, such as for example FitzMill®.

2. Benzothiazole 1,3 benzothiazol-2-yl-[2-(4-morpholin-4-ylmethyl-benzyloxy)-pyrimidin-4-yl]-acetonitrile, (Compound A) was synthesized as described in Example 1 of WO 03/047570. Compound A is used as a mesylate salt form having a molecular weight of 649.75 Da, with a salt/base ratio of 1.42 (the molecular weight of Compound A as a free base is 457.55 Da).

3. Excipients:

Gelucire® 50/13 (Stearoyl macrogol-32 glycerides) is synthesized by an alcoholysis/esterification reaction using hydrogenated palm oil and PEG-1 500 as starting materials. Gelucire® 50/13 is commercially available from Gattefossé. The predominant fatty acid is palmitostearic acid ($C_{16}$-$C_{18}$). Gelucire® 50/13 conforms to the European Pharmacopeia $4^{rd}$ edition related to "Stearoyl macrogolglycerides".

Typical properties of Gelucire® 50/13 are listed below:

Melting range (drop point): 46.0 to 51.0° C.

HLB value: 13.

4. Macrogol Glyceride Composition (1)

Stearoyl macrogol glyceride composition (1) has the following composition:

| | |
|---|---|
| Compound A (mesylate salt) | 20% w/w |
| Gelucire ® 50/13 | 80% w/w |

Composition (1) was manufactured according to the general procedure from Example 1, §1 and wherein 4 g of powder of Compound A and 16 g of powder of Gelucire® 50/13 were used and melting of the Gelucire® matrix was performed in a thermostated bath at 60° C.

5. Physico-Chemical Characteristics 5.1. Drug Content

Drug content of composition (1) measured by RP-HPLC analysis as described below was 20.11%, cv: 3.49%.

The stability of the formulation has been evaluated through the drug content for either a storage at 4° C. or at 25° C. over three months. Composition (1) was found to be stable as shown by the drug content after 3 months: 19.39%, cv: 0.35% (storage at 4°) and 19.51%, cv: 0.91% (storage at 25° C.).

RP-HPLC Analysis

Drug-loaded lipid matrices are completely dissolved in methanol, in ultrasonic bath for 2 min at room temperature. Samples are then centrifuged at 10.000 for 5 min at 10° C. The so-obtained clear solutions are analysed by RP-HPLC.

The RP-HPLC analysis used is performed on an isocratic HPLC Column: XterraMSC8, 5 µm, 250×4.6 mm (Waters) thermostated at 30° C.; Mobile phase: $H_2O$ $KH_2PO_4$ 20 mM-ACN 70% (% v/v)-30% (% v/v), adjusted at pH 4 with $H_3PO_4$ 10% at 1.2 ml/min. Compound A elutes at around 7 min.

5.2. Thermal Analysis

DSC analysis as described below was performed in order to check the homogeneity of the mixture and the stability of the drug when included in the matrix. Thermal behaviour of "Blanks" (Gelucire® matrix alone or Compound A alone) are compared to that of benzothiazole-loaded Gelucire® matrix (composition (1))

The DSC analysis indicates that the mixture is very homogeneous and that no change occurs in Compound A melting peak. It shows that Compound A is dispersed within the macrogol matrix mostly under crystalline form (about 85% of crystallinity maintained as calculated by measuring the ratio of enthalpy values of melting peaks of pure compound A vs. compound A dispersed in the formulation matrix).

DSC Analysis

The DSC analyses were performed in both heating and cooling mode, using the Pyris 1 Differential Scanning Calorimeter (Perkin Elmer), at the following operative conditions:

Sample mass: 1-5 mg
Range: 0° C.-250° C.
Scan rate: 5° C./min
Pan capacity: 50 µL (pan with holes)
Purge gas ($N_2$) flow: 20 cc/min.

Example 2

Benzothiazole Macrogol Glyceride Formulation (2)

1. General Preparation Procedure

Composition (2) is prepared as described in Example 1, §1, wherein suitable amount of 40% w/w benzothiazole calculated on the total composition was dispersed into the molten excipient.

2. Benzothiazole

Compound A described in Example 1, §1 was used.

3. Excipients:

3.1. Gelucire® 50/13 (Stearoyl Macrogol-32 Glycerides)
Gelucire® 50/13 described in Example 1, §1 was used.

4. Macrogol Glyceride Composition (2)

Stearoyl macrogol glyceride composition (2) has the following composition:

| | |
|---|---|
| Compound A (mesylate salt) | 40% w/w |
| Gelucire ® 50/13 | 60% w/w |

Composition (2) was manufactured according to the general procedure from Example 2, §1 and wherein 2 g of powder of Compound A and 3 g of powder of Gelucire® 50/13 were used and melting of the Gelucire® matrix was performed in a thermostated bath at 60° C.

5. Physico-Chemical Characteristics 5.1. Drug Content

Drug content was measured by RP-HPLC as described above. The drug content of composition (2) was 39.90%, cv: 1.26%.

The stability of the formulation has been evaluated through the drug content for either a storage at 4° C. or at 25° C. over two months. Composition (2) was found to be stable as shown by the drug content after 2 months: 39.76%, cv: 2.56% (storage at 4° C.) and 38.56%, cv: 1.09% (storage at 25° C.).

5.2. Thermal Analysis

DSC analysis as described above was performed and no significant changes in thermal behaviour of the formulation were detected over at least 7 months.

Example 3

Benzothiazole Macrogol Glyceride Formulation (3)

1. General Preparation Procedure

Composition (3) is prepared as described in Example 1, §1, wherein a mixture 50:50 w/w mixture of Gelucire® and Poloxamer is melted in a thermostated water bath and a suitable amount of benzothiazole (20% w/w calculated on the total composition) was dispersed into the molten excipient.

2. Benzothiazole

Compound A described in Example 1, §1 was used.

3. Excipients:

3.1. Gelucire® 50/13 (Stearoyl Macrogol-32 Glycerides)
Gelucire® 50/13 described in Example 1, §1 was used.

3.2. Lutrol® F68 (Poloxamer 188, Pluronic, Synperonic)

Lutrol® F68 (polyoxyethylene-polyoxypropylene block copolymer), commercially available from BASF, is a Block Copolymer of poly-ethylene-oxide and poly-propylene-oxide. Included in the FDA inactive Ingredients Guide (i.v. injections, inhalations, ophthalmic preparations, oral powder, solutions, suspensions and syrup, also topical preparations). Included in non-parenteral medicines licensed in the UK. European Pharmacopoeia 4, p 1777; USP 24 NF19 p 2492-2493.

In Pluronic® F68, the percentage of polyoxyethylene (hydrophilic) is 80%, and the molecular weight of the hydrophobe (polyoxypropylene) is approximately 1,967 Da.

Typical Properties of Pluronic® F68 are Listed Below:

Average Molecular Weight: 8400;
Melt/pour point: 52° C.;
Physical Form @20° C.: solid;
Viscosity (Brookfield) cps: 1000 [liquids at 25° C., pastes at 60° C. and solids at 77° C.];
Surface tension, dynes/cm @25° C.;
0.1% Conc.: 50.3
0.01% Conc.: 51.2
0.001% Conc.: 53.6
Interfacial tension, dynes/cm @25° C. vs Nujol;
0.1% Conc.: 19.8
0.01% Conc.: 24.0

0.01% Conc.: 26.0
Draves Wetting, Seconds 25° C.
1.0% Conc.: >360
0.1% Conc.: >360
Foam Height
Ross Miles, 0.1%, mm @50° C.: 35
Ross Miles, 0.1%, mm @26° C.: 40
Dynamic, 0.1%, mm @400 mL/min: >600
Cloud point in aqueous solution, ° C.
1% Conc.: >100
10% Conc.: >100
HLB (hydrophile-lipophile balance): 29.
4. Macrogol Glyceride Composition (3)
Stearoyl macrogol glyceride composition (3) has the following composition:

| Compound A (mesylate salt) | 20% w/w |
| Gelucire ® 50/13 | 40% w/w |
| Lutrol ® F68 | 40% w/w |

Composition (3) was manufactured according to the general procedure from Example 2, §1 and wherein 1.2 g of powder of Compound A, 2.4 g of powder of Gelucire® 50/13 and 2.4 g of Lutrol® F68 were used and melting of the Gelucire® matrix was performed in a thermostated bath at 60° C.
5. Physico-Chemical Characteristics
5.1. Drug Content
Drug content was measured by RP-HPLC as described above. The drug content of composition (3) was 18.99%, cv: 2.16%.
5.2. Thermal Analysis
DSC analysis as described above was performed and the same conclusions as in Example 1 were drawn.

Example 4

Benzothiazole Macrogol Glyceride Formulation (4)

1. General Preparation Procedure
Composition (4) is prepared as described in Example 1, §1, wherein a mixture 50:50 w/w mixture of Gelucire® and polyethylene (PEG) is melted in a thermostated water bath and a suitable amount of benzothiazole (20% w/w calculated on the total composition) was dispersed into the molten excipient.
2. Benzothiazole
Compound A described in Example 1, §1 was used.
3. Excipients:
3.1. Gelucire® 50/13 (Stearoyl Macrogol-32 Glycerides)
Gelucire® 50/13 described in Example 1, §1 was used.
3.2. Lutrol® E6000 (Polyethylene Glycol)
Lutrol® E6000, commercially available from BASF, is a high molecular weight polymer of ethylene oxide and a blend of polymers with different degrees of polymerization.
Typical Properties of Lutrol® E6000 are Listed Below:
Molecular weight: 5400-6600
Hydroxyl value: 16-22
Solidification point: 55-61° C.
Viscosity (50% aqueous solution; 20° C.): 200-270 mPa·s
PH (5% water): 4.5-7.5
Water content, by K. Fisher: ≦0.2%.
4. Macrogol Glyceride Composition (4)
Stearoyl macrogol glyceride composition (4) has the following composition:

| Compound A (mesylate salt) | 20% w/w |
| Gelucire ® 50/13 | 40% w/w |
| Lutrol ® E6000 | 40% w/w |

Composition (4) was manufactured according to the general procedure from Example 2, §1 and wherein 1.2 g of powder Compound A, 2.4 g of powder of Gelucire® 50/13 and 2.4 g of Lutrol® E6000 powder were used and melting of the Gelucire® matrix was performed in a thermostated bath at 60° C.
5. Physico-Chemical Characteristics
5.1. Drug Content
Drug content was measured by RP-HPLC as described above. The drug content of composition (4) was 20.26%, cv: 2.85%.
5.2. Thermal Analysis
DSC analysis as described above was performed and the same conclusions as in Example 1 were drawn.

Example 5

Macrogol Glyceride Composition (5)

1. General Preparation Procedure:
A concentrated aqueous solution of a benzothiazole according to Formula (I) was prepared. The benzothiazole solution was then incorporated, by vigorous stirring, into Gelucire® 50/13 molten matrix. The so-obtained emulsion was subsequently atomized with different nozzle types using the Liquid $CO_2$ atomization technology. The resulting microspheres are optionally submitted to drying (e.g. freeze-drying) to remove residual water from microspheres product if necessary.
2. Benzothiazole
Compound A described in Example 1, §1 was used.
3. Excipients:
3.1. Gelucire® 50/13 (Stearoyl Macrogol-32 Glycerides)
Gelucire® 50/13 described in Example 1, §1 was used.
4. Macrogol Glyceride Composition (5)
Stearoyl macrogol glyceride composition (5) has the following composition:

| Compound A (mesylate salt) | 5% w/w |
| Gelucire ® 50/13 | 95% w/w |

Composition (5) was manufactured according to the general procedure from Example 5, §1 and wherein 5 mL of a concentrated water solution of Compound A (200 mg/mL) is prepared and poured into 18 g of molten Gelucire® 50/13 under vigorous stirring (vortex). Melting of the Gelucire® matrix was performed in a thermostated bath at 70° C.
Two batches were prepared, one obtained by using atomisation with a capillary flow nozzle (Particle size by Optical Microscopy: 100-200 µm diameter) and the other one obtained by using atomisation with a nebulizing nozzle (Particle size by Optical Microscopy: 50-100 µm diameter).
The atomisation technique used was the atomisation method described in WO 2005/049192 under the following conditions:
Batch Prepared with Capillary Flow Nozzle:
Product nozzle diameter (capillary flow)=0.25 mm
Liquid $CO_2$ nozzle diameter=0.25 mm Product nozzle temperature=90° C.
Oven temperature=75° C.
Gaseous $CO_2$ pressure in the feeding vessel=2.7 bar
Liquid $CO_2$ pressure=about 60 bar.
Batch Prepared with Nebulizing Nozzle:
Liquid $CO_2$ nozzle diameter=0.25 mm
Product nozzle temperature=90° C.
Oven temperature=75° C.
Gaseous $CO_2$ pressure in the feeding vessel=2.7 bar
Gaseous $CO_2$ pressure in the product nozzle=5 bar
Liquid $CO_2$ pressure=about 60 bar.

5. Physico-Chemical Characteristics 5.1. Drug Content

Drug content was measured by RP-HPLC as described above. The drug content of composition (5) was 4.87%.

5.2. Thermal Analysis

The DSC analysis indicates that the Compound A is dispersed into the macrogol glyceride matrix in a non-crystalline form (amorphous form or solid molecular solution) as DSC analysis indicates none or minimal residual crystallinity (less than 5%).

5.3. Particle Size

Optical microscope images shows that the drug loaded particles have a mean size around 50 to 200 μm diameter, depending on the type of nozzle used.

Example 6

Solubilization of Benzothiazole Macrogol Glyceride Formulations

The benzothiazole macrogol glyceride formulations (1), (2), (3), (4) and the bulk (compound A) were compared for their drug solubilization profile in FeSSIF (Fed State Simulated Intestinal Fluid, pH=5), in oversaturated conditions as described in the protocol below.

The solubilization profiles in oversaturated conditions, presented in FIG. 1, show that the amount of compound A initially dissolved (i.e. within the first 2 hours) from macrogol glyceride formulations of the invention is much higher than the one dissolved from bulk in the same time interval.

The benzothiazole macrogol glyceride formulation (5) prepared by atomisation, The benzothiazole macrogol glyceride formulation (1) prepared by cryo-micronization and the bulk (Compound A) were compared for their solubilization profile in FeSSIF (Fed State Simulated Intestinal Fluid, pH=5), in oversaturated conditions.

Figure 2:
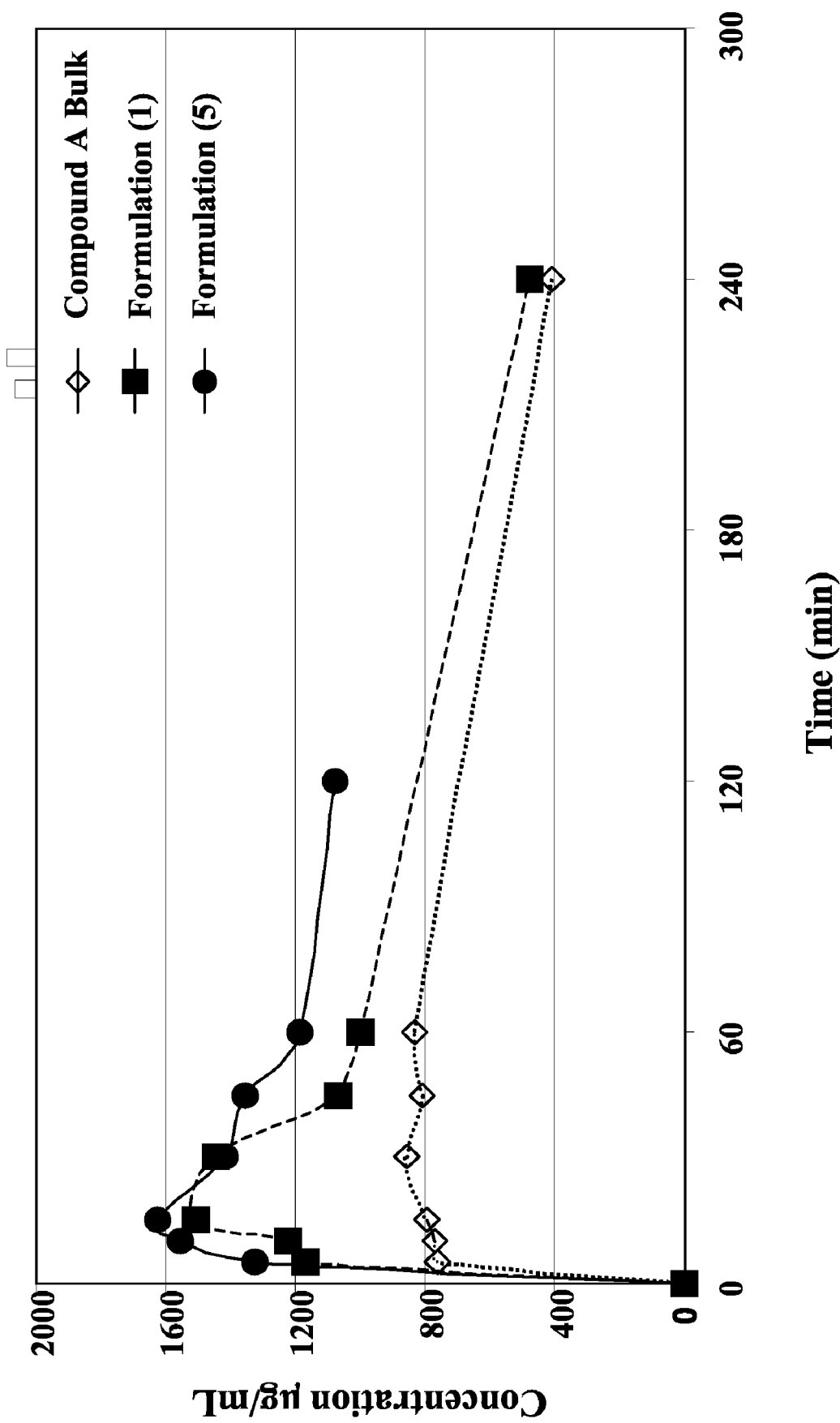
FIG. 2 shows the solubilization profile (expressed as concentration (μg/mL) versus time (min)) in oversaturation conditions, Fed State Simulated Intestinal Fluid (FeSSIF), pH=5 as dissolution medium) of Compound A in different solid powder (particles) formulations compared to bulk powder. Open lozenges: Compound A, solid bulk; Filled squares: Compound A, macrogol glyceride solid formulation (1); Filled circles: Compound A, macrogol glyceride solid formulation (5).

The solubilization profiles presented in FIG. 2, show that the macrogol glyceride formulation (5) has a higher and more prolonged drug solubilization than the cryomicronized one (2) and both are very superior to the bulk.

The improved solubilization profiles of Gelucire formulations (1) to (5) compared to bulk show that Gelucire formulations improve the solubilization of benzothiazoles according to the invention.

The improved solubilization profile of the atomized formulation (5) prepared by a process which favours dispersion of the Compound A within the macrogol glyceride in an amorphous state, indicates that an even higher drug concentration can be reached in FeSSIF solution, and therefore allowing more drug to be available for absorption.

Solubilization Kinetics in Oversaturated Conditions:

Weighed amounts of macrogol glyceride formulations of Compound A, in powder form, or of Compound A, bulk powder were added under stirring, in order to constantly maintain in the dissolution medium a large excess of Compound A (much higher than the solubility reachable at the equilibrium). Samples of dissolution medium were withdrawn at different time points and analyzed for Compound A concentration.

Glass beaker with magnetic stirring (320 rpm)
Medium: Fed State Simulated Intestinal Fluid pH=5 (50 mL)
Temperature: 37° C.
Oversaturated conditions: 4 mg/mL (Theoretical maximum amount of Compound A added to the dissolution medium, indicating the excess of compound A).

The benzothiazole macrogol glyceride formulations (1), (2), (3) and the bulk (Compound A) were compared for their dissolution profile in FeSSIF pH 5, in sink conditions, according to the USP XXVII Drug Dissolution Method II (Paddle), as described in the protocol below.

Drug Dissolution Test measures the drug dissolved and thus released from the solid bulk or from the formulations in the dissolution medium, in conditions below the solubility at equilibrium ("sink conditions"); the amount of Compound A is expressed as % of total amount of drug released in the dissolution vessel vs. total amount of drug added to it at $t_0$.

Figure 3:
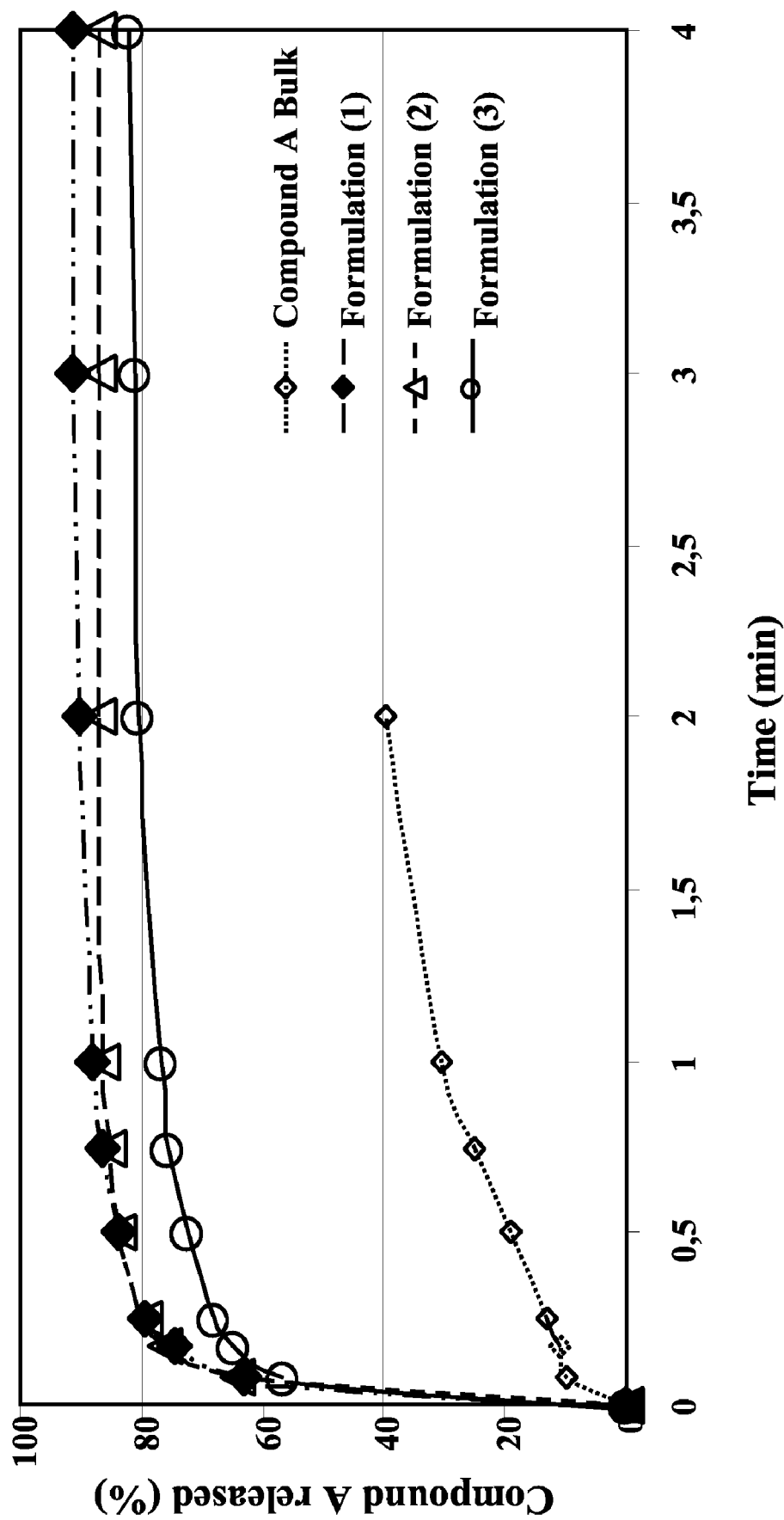
FIG. 3 represents the dissolution profile of Compound A from different solid powder formulations, compared to solid bulk, obtained with the USP Dissolution Method II (Paddle), in FeSSIF, pH 5, sink conditions. Open lozenges: Compound A, in solid bulk; Filled lozenges: Compound A, macrogol glyceride solid formulation (1); Open triangles: Compound A, macrogol glyceride solid formulation (2); Open circles: Compound A, macrogol glyceride solid formulation (3).

The dissolution profile presented in FIG. 3, show a very relevant improvement in drug dissolution rate for the formulations of the invention.

Two batches of benzothiazole macrogol glyceride formulations (5)—one prepared with a capillary nozzle, the other with the nebulizing nozzle—and the bulk (compound A)—were compared for their dissolution profile in FeSSIF, pH 5 in sink conditions, according to the USP XXVII Drug Dissolution Method II (Paddle), as described in the protocol below.

Drug dissolution rate from benzothiazole macrogol glyceride formulation (5) was substantially improved compared to the drug bulk. Moreover, differences in drug dissolution profile are detectable between microspheres prepared with different nozzles, with more effective drug dissolution reached by smaller size microspheres produced by nebulizing nozzle.

Dissolution Rates in Sink Conditions:

Weighed amounts of macrogol glyceride formulations of Compound A, in powder form, or of Compound A bulk powder were added into a measured volume of dissolution medium, contained in vessels of a USP XXVII Drug Dissolution Apparatus, Type II (Paddle). Sink conditions were calculated as below reported.

USP XXVII Drug Dissolution Method II (Paddle)
Paddle speed: 100 rpm
Medium: Fed State Simulated Intestinal Fluid pH=5 (200 mL)
Temperature: 37° C.
Sink conditions: <0.2 $c_s$ ($c_s$=Concentration of the drug solution in presence of drug excess, after 24 h at room temperature).

Example 7

Pharmacokinetic Profile of Benzothiazole Macrogol Glyceride Formulations

Macrogol Glyceride formulations were orally administered in Beagle dogs as extemporaneous suspension in PBS at a dose of 10.6 mg/kg following the protocol below, by gavage in a volume of 2 mL/kg and bulk formulation by forced introduction into the throat.

The formulations were administered to the animals which had fasted overnight (i.e. for about 16 hours) before treatment, food was allowed again 4 hours after treatment.

Macrogol Glyceride formulations (1) and (2) were orally administered as described above. A wash-out interval between the administration of formulation (1) and of formulations (2) was of at least 1 week.

6 Beagle dogs (3 males and 3 females) of about 10-13 kg of bodyweight and of age 9 to 12 months were used. Animals were weighed fasted before administration and the body weight recorded.

The following experimental design was followed:

|  | Period 1 | Period 2 |
|---|---|---|
| Route | oral | oral |
| Dose (mg/kg) | 10.6 | 10.6 |
|  | (Formulation 1) | (Formulation 2) |

Blood and Plasma Collection

Blood (at least 2.5 ml) was collected from a jugular vein into heparinised tubes before and after dosing, at the following 15 times:

0 (pre-dose), 0.25, 0.5, 1, 1.5, 2, 3, 4, 5, 6, 8, 12, 24, 32 and 48 hours after administration.

Blood was centrifuged within 15 min at about 2500 g at +4° C. for 10 min. Blood cells were discharged and plasma obtained was divided into 3 aliquots (at least 0.3 mL each). The plasma concentrations of Compound A (free base of Compound A, mesylate) in the unknown dog plasma samples was determined by a High Performance Liquid Chromatography/Mass Spectrometry (HPLC/MS).

The following pharmacokinetic parameters were obtained or calculated from the individual plasma concentrations of Compound A vs time after administration using WinNonlin-program version 3.1 (Pharsight Corporation, Palo Alto, Calif., USA):

Cmax: The highest concentration value found.
tmax: The time from administration at which the Cmax value is found.
tz: The last sampling time at which a detectable concentration is found.
Cz: The concentration value obtained at sampling time tz.
AUCz: The area under the plasma concentration vs time curve up to sampling time tz, calculated by the log-linear trapezoidal rule.
t½: The terminal half-life.
AUC: The area under the plasma concentration vs time curve extrapolated to infinity.
F: The absolute bioavailability for oral routes calculated as ratio of the normalized AUC. Intravenous AUC, from the pharmacokinetic study in dog with bulk compound A is used.

Figure 4:
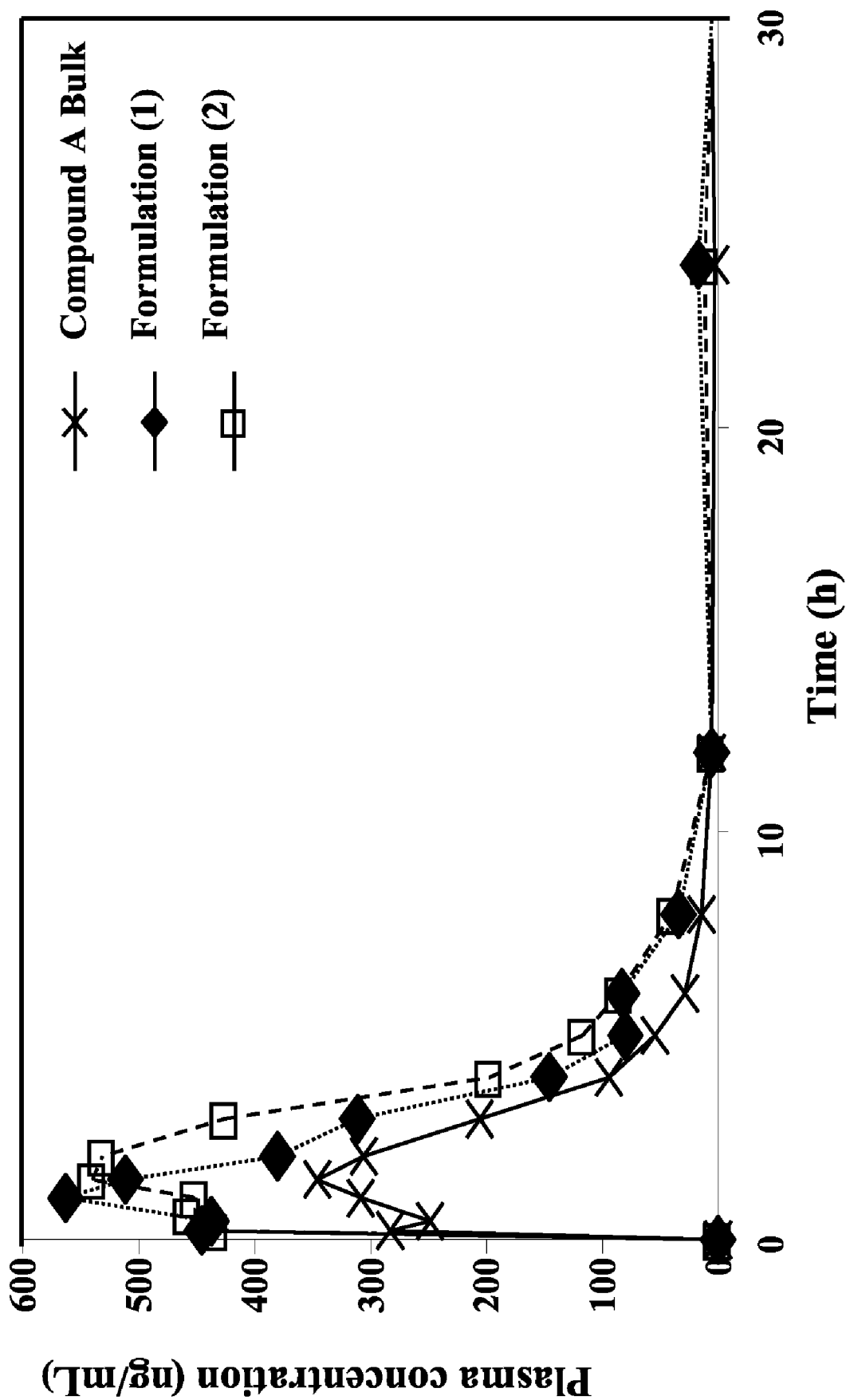
FIG. 4 represents the plasma concentration (ng/mL) of compound A after oral administration in dogs of a 10.6 mg/kg dose, as formulations of the invention compared to solid bulk after extemporaneous suspension in PBS. Cross: Compound A, bulk suspension; Filled lozenges: Compound A, macrogol glyceride formulation suspension (1); Open squares: Compound A macrogol glyceride formulation suspension (2).

The pharmacokinetic results presented in FIG. 4 show that the oral absorption of Compound A, is strongly increased when administered in macrogol glyceride formulations according to the invention, the bioavailability being increased from less than 15% (Compound A in Water for Injection) to about 30% and above (formulations (1) and (2)).

Compounds of Examples 8-28 were synthesized according to the methods described in Schemes I to VIII above.

The HPLC, NMR and MS data provided in the examples described below were obtained as followed: HPLC: column Waters Symmetry C8 50×4.6 mm, Conditions: a-MeCN/H$_2$O 0.09% TFA, 0 to 100% (10 min); b-MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The purifications were obtained as followed: Preparative HPLC Waters Prep LC 4000 System equipped with columns Prep Nova-Pak®HR C18 6 μm 60 Å, 40×30 mm (up to 100 mg) or 40×300 mm (up to 1 g). All the purifications were performed with a gradient of MeCN/H$_2$O 0.09% TFA.

Intermediate 1: Preparation of 1,3-benzothiazol-2-yl (2-chloro-4-pyrimidinyl)-acetonitrile

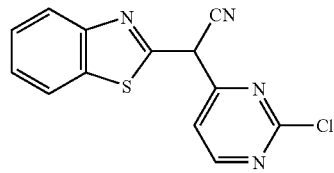

To a stirred suspension of NaH (60% in oil, 9.2 g, 0.23 mol) in dry THF (200 ml) was added drop wise under inert atmosphere a solution of 1,3-benzothiazol-2yl-acetonitrile (20 g, 0.15 mol) in dry THF (200 ml). After 1 h 30 stirring at r.t., a solution of 2,4-dichloropyri-midine (17.1 g, 0.15 mol) in dry THF (200 ml) was added dropwise. The reaction mixture was allowed to stir under inert atmosphere at r.t. until complete disappearance of the starting material. The reaction was quenched by addition of water and the THF was evaporated. Water was added and the suspension was slightly acidified with aqueous HCl 1M. The precipitate obtained was filtered off and washed thoroughly with water until neutral then with hexane to remove the oil. The crude solid was dried under vacuum at 40° C., affording 28 g (84%) of the title compound as a light brown powder: mp 246° C. dec.; MS: 286.8 (M+1); HPLC (Conditions a, 268 nm) 97%, rt. 5.66 min; $^1$HNMR (DMSO-d6) δ 13.25 (br s, 1H, exchangeable), 8.09 (d, J=4.14 Hz, 1H), 7.90 (d, J=7.53 Hz, 1H), 7.61 (d, J=7.92 Hz, 1H), 7.39-7.34 (m, 1H), 7.20-7.15 (m, 1H), 6.96 (br d, 1H). CHN analysis: C$_{13}$H$_7$ClN$_4$S: Calculated: C, 54.19%; H, 2.48%; N, 19.45%. Found: C, 53.35%; H, 2.77%; N, 17.62%.

Intermediate 2: Preparation of (3-Morpholin-4-ylmethyl-phenyl)-methanol

Step 1: Methyl-m-toluate

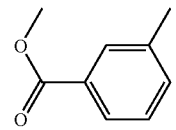

To a solution of m-toluic acid (175 g, 1.28 mol) in methanol (2 L) was added dropwise thionylchloride (612 g, 5.14 mol) under stirring at 5° C. The mixture was refluxed overnight, then the solvent evaporated. The residue obtained was treated with a 10% aqueous NaHCO$_3$ solution (pH ~8). The product was extracted with ethyl acetate, washed with water and dried. The solvent was removed and the crude was purified by column chromatography (pet ether/ethyl acetate) to give methyl-m-toluate as colorless liquid (180 g, 93%).

Step 2: methyl 3-(bromomethyl)benzoate

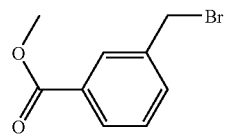

To a mixture of methyl-m-toluate (180 g, 1.2 mol) and N-bromosuccimide (235 g, 1.32 mol) in CCl4 (2 L) was added in portion benzoyl peroxide (18 g, 0.1 times) at 50° C. The mixture was refluxed for 5 h. Then the mixture was allowed to cool down to 40° C. and the solid was filtered off. The filtrate was concentrated to give methyl 3-(bromomethyl) benzoate (252 g, 91%) as light yellow liquid.

Step 3: methyl 3-(morpholin-4-ylmethyl)benzoate

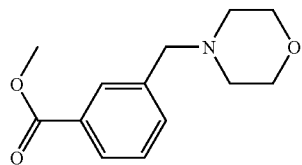

To a solution of morpholine (80 g, 0.91 mol) and triethylamine (232 g, 2.29 mol) in EtOH (1750 ml) was added dropwise at 0° C. a solution of methyl 3-(bromomethyl)benzoate (252 g, 1.1034 mol) in absolute alcohol (250 ml). The mixture was stirred overnight at RT. Then the mixture was concentrated and the residue obtained was taken up in 1.5N HCl (3 L) then washed with diethyl ether (3 times) and ethyl acetate. The solution was neutralized with a 10% aqueous NaOH solution and basified up to pH=8 with a 10% aqueous NaHCO$_3$ solution. The product was extracted with CHCl$_3$, washed with water and brine then dried over Na$_2$SO$_4$. The solvent was removed and the crude was purified by column chromatography CHCl$_3$/MeOH to give methyl 3-(morpholin-4-ylmethyl)benzoate (150 g, 70%) as brown liquid.

Step 4: (3-Morpholin-4-ylmethyl-phenyl)-methanol

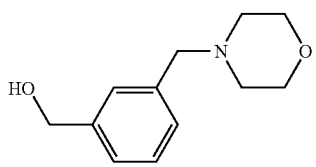

To a mixture of LAH (36 g, 0.95 7 mol) in dry THF (1750 ml) was added dropwise at 0° C. under N$_2$ a solution of N-(3-methoxycarbonyl benzyl)bromide (150 g, 0.638 mol) in dry THF (250 ml). The mixture was stirred overnight at RT under N$_2$, then quenched with a 10% aqueous NaOH solution. The solid was filtered off and the filtrate was concentrated. The residue was taken up in DCM (1 L) and washed with water. The solvent evaporated to give N-(3-hydroxymethylbenzyl)morpholine (96 g, 73%) as light yellow liquid. $^1$H NMR (DMSO-d6) δ 7.28-7.23 (m, 2H), 7.19-7.13 (m, 2H), 5.14 (t, J=5.65 Hz, 1H), 4.47 (d, J=5.84 Hz, 2H), 3.57-3.54 (m, 4H), 3.42 (s, 2H), 2.34-2.31 (m, 4H).

Upon using this procedure described above in the example T and the appropriate starting material and reagents, the following additional para or meta substituted benzyl alcohol derivatives could be obtained.

Intermediate 3:
(3-Piperidin-1-ylmethyl-phenyl)-methanol

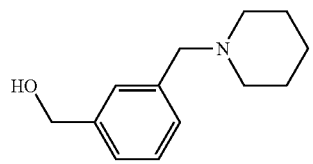

$^1$H NMR (DMSO-d6) δ 7.26-7.21 (m, 2H), 7.17-7.11 (m, 2H), 5.14 (t, J=5.65 Hz, 1H), 4.47 (d, J=5.65 Hz, 2H), 3.38 (s, 2H), 2.32-2.25 (m, 4H), 1.60-1.36 (m, 6H).

Intermediate 4:
(3-(4-Methyl-piperazin-1-ylmethyl-phenyl)-methanol

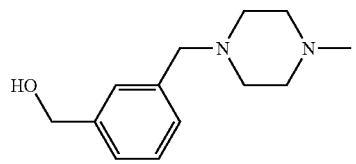

$^1$H NMR (DMSO-d6) δ 7.27-7.11 (m, 4H), 5.17-5.13 (m, 1H), 4.48-4.46 (m, 2H), 3.41 (s, 2H), 2.41-2.21 (m, 8H), 2.13 (s, 3H).

Intermediate 5:
(3-Imidazolyl-1-ylmethyl-phenyl)-methanol

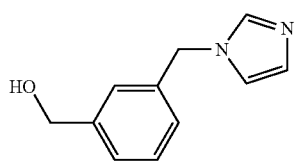

$^1$H NMR (DMSO-d6) δ 7.73 (s, 1H), 7.32-7.20 (m, 3H), 7.16-7.15 (m, 1H), 7.12-7.09 (m, 1H), 6.87 (s, 1H), 5.20 (t, J=5.65 Hz, 1H), 5.17 (s, 2H), 4.46 (d, J=5.65 Hz, 2H).

Intermediate 6: (4-(2, 6-Dimethyl-morpholin-4-ylm-ethyl)-phenyl)-methanol

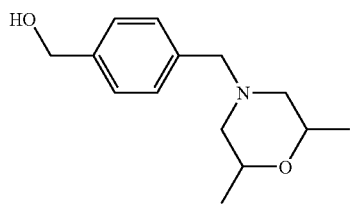

M$^+$(ES):236.0. $^1$H NMR (DMSO-d6) δ 7.7-7.20 (m, 4H), 5.12 (t, J=5.7 Hz, 1H), 4.46 (d, J=5.7 Hz, 2H), 3.56-3.50 (m, 2H), 3.39 (s, 2H), 2.65-2.61 (m, 2H), 2.50-2.48 (m, 1H), 1.64-1.57 (m, 2H), 1.01 (s (s, 3H), 0.99 (s, 3H).

Intermediate 7: (4-((Bis-(2-methoxy-ethyl)-amino)-methyl)-phenyl)-methanol

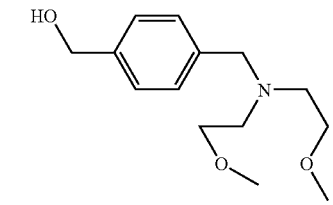

M$^+$(ES): 254.2. $^1$H NMR (DMSO-d6) δ 7.23 (s, 4H), 5.11 (t, J=5.65 Hz, 1H), 4.45 (d, J=5.65 Hz, 2H), 3.59 (s, 2H), 3.40-3.36 (m, 4H), 3.19 (s, 6H), 2.61-2.57 (m, 4H).

Intermediate 8: (4-(4-tert-Butoxy-piperidin-1-ylm-ethyl)-phenyl)-methanol

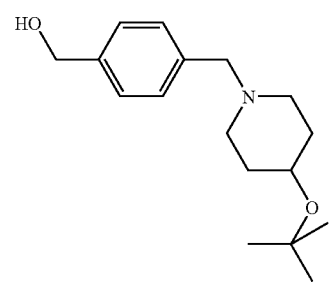

M$^+$(ES): 278.2. $^1$H NMR (DMSO-d6) δ 7.25-7.18 (m, 4H), 5.11 (t, J=5.65 Hz, 1H), 4.45 (d, J=5.65 Hz, 2H), 3.47-3.38 (m, 2H), 2.65-2.62 (m, 2H), 2.05-1.98 (m, 2H), 1.64-1.58 (m, 2H), 1.41-1.29 (m, 2H), 1.10 (s, 9H).

Intermediate 9: (4-(3,4-Dihydro-1H-isoquinolin-2-ylmethyl)-phenyl)-methanol

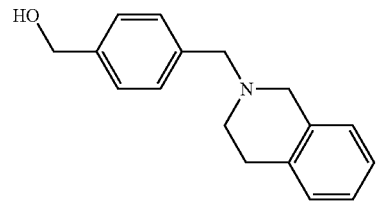

$^1$H NMR (DMSO-d6) δ 7.31-7.25 (m, 4H), 7.09-7.03 (m, 3H), 6.98-6.96 (m, 1H), 5.14 (t, J=5.47 Hz, 1H), 4.47 (d, J=5.47 Hz, 1H), 3.60 (s, 2H), 3.50 (s, 2H), 2.79 (t, J=5.65 Hz, 1H), 2.66-2.62 (m, 2H).

Intermediate 10: Preparation of Benzyl-(4-hydroxymethyl-benzyl)-carbamic acid tert-butyl ester Step 1: 4-(aminomethyl)benzoic acid

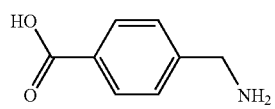

A mixture of 4-cyano benzoic acid (500 g, 3.4 mol) and Raney Nickel (100 g) in methanol (5 L) was hydrogenated at a pressure of 10 kg for 16 h. The catalyst was removed by filtration, followed by the removal of the solvent under reduced pressure to afford 4-(aminomethyl)benzoic acid (430 g, 84%) as a white solid.

Step 2: Methyl-4-(aminomethyl)benzoate

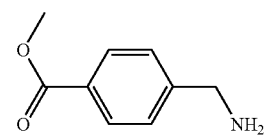

To a solution of 4-(aminomethyl)benzoic acid (300 g, 1.98 mol) in methanol (5 L) was added thionylchloride (473 g 3.97 mol). The reaction mixture was refluxed for 6 h, followed by the removal of the solvent under reduced pressure to obtain the crude product. The crude was purified by acid-base work up to afford methyl-4-(aminomethyl)benzoate (300 g, 92%) as a liquid.

Step 3: N-(4-Methoxycarbonylbenzyl)benzylamine

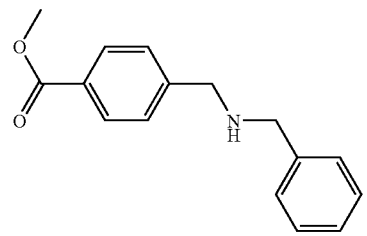

A mixture of methyl-4-(aminomethyl)benzoate (50 g, 0.302 mol) and benzaldehyde (32 g, 0.302 mol) in EtOH (1 L) was refluxed for 5 h. After cooling to r.t, NaBH₄ (11.5 g, 0.302 mol) was added portionwise. The reaction mixture was stirred at r.t. for 10 h. The solvent was removed under reduced pressure and the compound was purified by acid-base work up to give N-(4-methoxycarbonylbenzyl)benzylamine (25 g, 33%).

Step 4: 4-methoxy carbonyl-[N-(BOC)-N-[benzyl]benzylamine

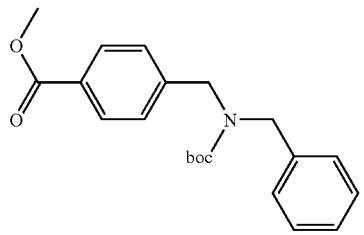

To a mixture of N-(4-methoxycarbonylphenyl)benylamine (25 g, 0.098 mol) in CH₂Cl₂ (500 ml), was added diisopropyl ethylamine (38 g, 0.294 mol) and (BOC)₂O (32 g, 0.147 mol). After stirring at r.t. for 5 h, the solvent was removed under reduce pressure. The crude product was then purified by chromatography using chloroform/methanol (9/1) to afford 4-methoxy carbonyl-[N-(BOC)-N-[benzyl]benzylamine (27 g, 78%) as a liquid.

Step 5: Tert-Butyl-N-[(4-hydroxymethyl)benzyl]-N-(benzyl)carbamate

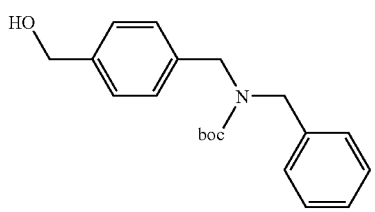

To a suspension of LAH (4 g, 0.105 mol) in dry THF (150 mL) was added a solution of 4-methoxy carbonyl-N-[Boc]-N-[benzyl]benzylamine (25 g, 0.070 mol) in dry THF (25 mL) with stirring at −40° C. The reaction mixture was slowly warmed up to r.t. and stirred for 2 h. Then it was quenched with 20 mL of 10% aqueous NaOH solution and the precipitate formed was filtered off. The filtrate was concentrated and the residue was purified by column chromatography (chloroform/methanol, 9:1) to give 16 g (65%) of the title compound as a liquid.

TLC—Chloroform/methanol (9/1): $R_f$=0.6. ¹H NMR (DMSO-d6) δ 7.50-7.00 (m, 9H), 5.15 (t, J=5.65 Hz, 1H), 4.48 (d, J=5.65 Hz, 2H), 4.40-4.15 (m, 4H), 1.40 (s, 9H).

Intermediate 11: Preparation of (2-Piperidin-1-yl pyridin-4-yl)methanol

Step 1: 2-Bromo-4-methylpyridine

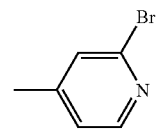

To a solution of 2-amino-4-methylpyridine (120 g, 1.1 mol) in 48% HBr (1.5 L) at −20° C. was added bromine (160 mL, 3.11 mol) dropwise. The reaction mixture was stirred for 3 h at −15° C. to −20° C. To the above mixture was added portionwise an aqueous solution of NaNO₂ (204 g, 2.95 mol). The reaction mixture was then allowed to warm to RT over a period of 3 h. A 20% aqueous NaOH (1.2 Kg of NaOH in 2 L water) solution was added and the pH was adjusted to 12 maintaining the temperature at 0° C. The reaction mixture was extracted with diethyl ether (3×250 mL), washed with water, brine and dried. The solvent was removed and purified by fractional distillation to afford 2-bromo-4-methylpyridine (164 g, 86%) as pale yellow liquid.

Step 2: 2-bromoisonicotinic acid

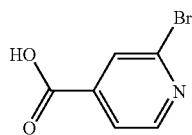

To a mixture of 2-bromo-4-picoline (300 g, 1.74 mol) in pyridine/water (1 L each) at 95° C. was added KMnO₄ (200 g) dissolved in water (IL). Further, added KMnO₄ (2 Kg) in portions (app. 20 mg each time) over a period of 4 days. The reaction mixture was cooled to RT and filtered off the solid MnO₂. The filtrate was evaporated completely under reduce pressure and acidified with 6N HCl. The solid product obtained was filtered, washed with water and dried to give 2-bromoisonicotinic acid (166 g, 47%).

Step 3: 2-Piperidin-1-ylisonicotinic acid

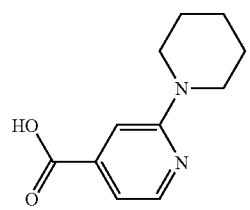

A mixture of 2-bromoisonicotinic acid (40 g, 0.198 mol) and piperidine (200 mL) was refluxed at 105° C. for 24 h under $N_2$ atmosphere. The excess piperidine was distilled under vacuum and crude residue was diluted with water (500 mL) and extracted with chloroform (3×250 mL), washed with brine and dried. The solvent was removed under vacuum to give 2-Piperidin-1-yl-isonicotinic acid (35 g, 85%) as a solid.

Step 4: methyl 2-piperidin-1-ylisonicotinate

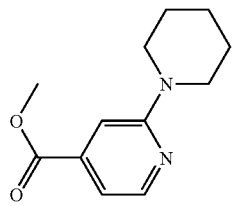

A mixture of 2-Piperidin-1-yl-isonicotinic acid (30 g, 0.145 mol) in methanol (500 mL) was cooled to 0° C. and then thionylchloride (42 mL) was added. The reaction mixture was refluxed for 20 h. The solvent was removed under vacuum and the residue was taken up in EtOAc (500 mL). The organic layer was washed with 10% aqueous $NaHCO_3$ solution, water, brine and dried. The solvent was removed under vacuum to methyl 2-piperidin-1-ylisonicotinate (18 g, 56%) as yellow liquid.

Step 5: (2-Piperidin-1-yl pyridin-4-yl)methanol

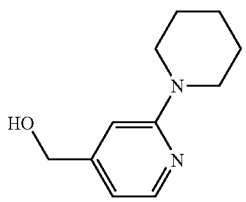

To a suspension of LAH (5.5 g, 0.145 mol) in dry THF (500 mL) at 0° C. was added methyl 2-piperidin-1-ylisonicotinate (18 g, 0.095 mol) in dry THF (100 mL) under $N_2$ atmosphere. The reaction mixture was stirred at RT for 4 h and quenched with 10% aqueous NaOH solution at −20° C. The solid was filtered off, washed with THF and concentrated. The residue was dissolved in $CH_2Cl_2$ (250 mL), washed with water, brine and dried. The solvent was removed under vacuum and the crude was purified by column chromatography over silica gel ($CHCl_3$/MeOH, 9:1) to give (2-piperidin-1-yl pyridin-4-yl)methanol (12 g, 65%). $^1H$ NMR (DMSO-d6) δ 7.98 (d, J=5.2 Hz, 1H), 6.71 (s, 1H), 6.51 (br d, 1H), 5.24 (t, J=5.2 Hz, 1H), 4.41 (d, J=5.2 Hz, 2H), 3.49-3.46 (m, 4H), 1.58-1.50 (m, 6H).

In a similar way the following intermediate compounds may be obtained.

Intermediate 12:
N-(4-hydroxymethylpyridin-2-yl)morpholine

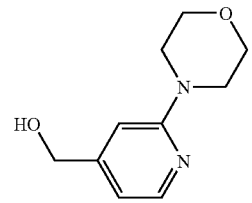

$^1H$ NMR (DMSO-d6) δ 8.04 (d, J=5.1 HZ, 1H), 6.74 (s, 1H), 6.62 (d, J=5.1 Hz, 1H), 5.29 (t, J=5.7 Hz, 1H), 4.43 (d, J=5.7 Hz, 2H), 3.69-3.66 (m, 4H), 3.41-3.38 (m, 4H).

Intermediate 13: Preparation of
(5-morpholin-4-ylpyridin-3-yl)methanol

Step 1: Methyl 5-morpholin-4-ylnicotinate

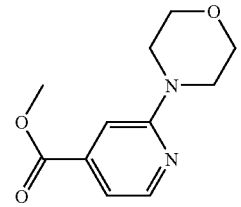

To a mixture of methyl-5-bromonicotinate (10 g, 0.045 mol) and morpholine (4.6 g, 0.054 mol) in dry toluene (100 mL) was added fused $CsCO_3$ (30 g, 0.09 mol) with stirring under argon. To this mixture was added BINAP (0.45 g, 0.0005 mol), $Pd_2(dba)_3$ (0.22 g, 0.00015 mol) and then the reaction mixture was refluxed at 110° C. for 50 h. The reaction mixture was cooled down to r.t. and diluted with diethyl ether (400 ml) and filtered through celite. The filtrate was concentrated under vacuum and purified by flash column chromatography ($CHCl_3$/MeOH, 4:1) to give 4.2 g (41%) of methyl 5-morpholin-4-ylnicotinate as a liquid. TLC—Chloroform/Methanol (8/2): $R_f$=0.7.

Step 2: (5-Morpholin-4-ylpyridin-3-yl)methanol

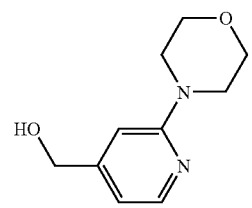

To a suspension of LAH (1 g, 0.027 mol) in dry THF (70 mL) was added methyl 5-morpholin-4-ylnicotinate (4 g, 0.018 mol) in dry THF (10 mL) at −40° C. under stirring. The reaction mixture was stirred at this temperature for 2 h and then quenched with 6 mL of 10% aqueous NaOH solution at −40° C. The reaction mixture was allowed to stir at RT for 30 min, filtered through celite, washed with THF and concentrated to afford 2.8 g, (80%) of the title compound as a liquid.

TLC—Chloroform/Methanol (8/2): R$_f$=0.55. $^1$H NMR (DMSO-d6) δ 8.17 (d, J=2.6 Hz, 1H), 7.97 (s, 1H), 7.23 (s, 1H), 5.24 (t, J=5.6 Hz, 1H), 4.47 (d, J=5.6 Hz, 2H), 3.75-3.72 (m, 4H), 3.15-3.12 (m, 4H).

Intermediate 14: 2-(4-methylpiperazin-1-yl)ethanol

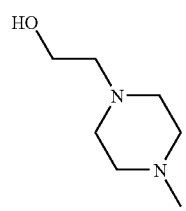

In THF (30 ml) were added N-(2-hydroxyethyl)piperazine (500 mg, 3.84 mmol), a solution of formaldehyde (3117 mg, 38.41 mmol) and sodium cyanoborohydride (1207 mg, 19.20 mmol). The mixture was heated up to 50° C. overnight under stirring. After cooling some water was added and the mixture was extracted with DCM (3×). The organic layers were dried over MgSO4 and evaporated. The residue was purified over a silica plug with DCM/MeOH 9:1 as eluant to afford an oil (370 mg, Y=67%). $^1$H NMR (DMSO-d6) δ 4.45 (t, J=5.3 Hz, 1H), 3.51-3.45 (m, 2H), 3.02-2.84 (m, 4H), 2.71-2.64 (m, 2H), 2.61 (s, 3H), 2.58-2.53 (m, 2H), 2.47-2.43 (m, 2H).

Intermediate 15: {4-[(4-methylpiperazin-1-yl)carbonyl]phenyl}methanol

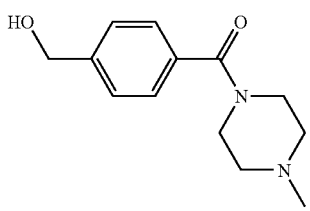

To a solution of N-methyl piperazine (3.33 ml, 30.09 mmol) was added a solution of trimethylaluminium in heptane (15.04 ml, 30.09 mmol) and the mixture was stirred 10 min at room temperature. To this solution was added a solution of 4-(hydroxymethyl)benzoic acid methyl ester (1000 mg, 6.02 mmol) in DCE and the mixture was refluxed under inert atmosphere for 3 h. The mixture was diluted with DCM then water was added. The suspension was filtered through celite. The filtrate was washed with a solution 5% of NaHCO3 (2×) then water and brine. The organic layers were dried over MgSO4, evaporated and dried at 40° C. under vacuum to afford 307 mg (Y=21%) of the title compound as an oil. $^1$H NMR (DMSO-d6) δ 7.45-7.37 (m, 4H), 5.33 (t, J=5.6 Hz, 1H), 4.58 (br d, 2H), 3.77-3.50 (m, 4H), 2.46-2.30 (m, 4H), 2.26 (s, 3H).

Example 8

1,3-benzothiazol-2-yl[2-(2-pyridin-3-ylethoxy)pyrimidin-4-yl]acetonitrile

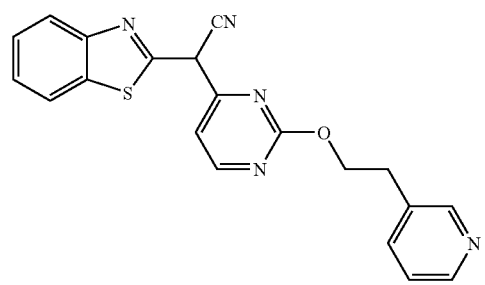

To a solution of intermediate 1 (0.200 g, 0.7 mmol) in DMA (3 ml) were added 3-(2-hydroxyethyl)pyridine (0.172 g, 1.4 mmol), cesium carbonate (1.14 g, 3.5 mmol) and copper iodide (0.133 g, 0.7 mmol) and the suspension was shaken at 100° C. for 19 days. After cooling to r.t., the solvent was evaporated. The residue was washed several times with water then filtered off and dried at 40° C. under vacuum. The solid was taken up in a mixture of DCM/TFA and ether was added. The precipitate formed was filtered off, washed with ether (3×). After purification by preparative HPLC and drying under vacuum at 40° C., 121 mg (29%) of the title compound was obtained as a yellow powder.

M$^-$(ESI): 371.8; M$^+$(ESI): 374.0; HPLC (Conditions b, max plot) 96.1%; Rt 1.89 min. $^1$H NMR (DMSO-d$_6$) δ 8.90 (very br d, 1H), 8.31 (br d, 1H), 7.88-7.73 (m, 4H), 7.45-7.40 (m, 1H), 7.30-7.26 (m, 1H), 6.67 (br d, 1H), 4.94 (br t, 2H), 3.36-3.32 (m, 2H). CHN analysis: $C_{20}H_{15}N_5OS$. 2 $C_2HF_3O_2.0.2H_2O$ Calculated: C, 47.64%; H, 2.90%; N, 11.57%. Found: C, 47.62%; H, 3.21%; N, 11.75%.

Example 9

1,3-benzothiazol-2-yl[2-(quinolin-6-yloxy)pyrimidin-4-yl]acetonitrile

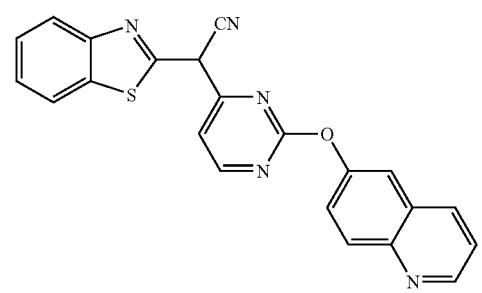

The title compound was obtained by performing the same protocol set out in the above Example 8, whereby 2-naphthol is used instead of 3-(2-hydroxyethyl)pyridine. Y=16%; M$^+$(ESI): 396.0; HPLC (Conditions a, max plot) 99.4%; Rt: 3.47 min. $^1$H NMR (DMSO-d$_6$) δ 9.06 (m, 1H), 8.51-8.48 (m, 1H), 8.26 (br d, 1H), 8.21 (d, J=9 Hz, 1H), 8.02 (d, J=2.3 Hz, 1H), 7.80 (dd, J=2.3 Hz, J=9 Hz, 1H), 7.69 (dd, J=4.1 Hz, J=8.3 Hz, 1H), 7.52 (d, J=7.9 Hz, 1H), 7.35-7.29 (m, 1H), 7.12-7.07 (m, 1H), 6.92 (br d, 1H), 6.64 (br d, 1H).

Example 10

1,3-benzothiazol-2-yl{2-[(5-morpholin-4-ylpyridin-3-yl)methoxy]pyrimidin-4-yl}acetonitrile

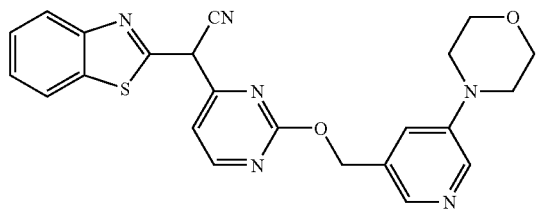

To a suspension of NaH (60% in oil, 245 mg, 6.14 mmol) in dry ACN (3 ml) was added a solution of (3-morpholin-4-ylphenyl)methanol (596 mg, 3.07 mmol) in dry ACN (3 ml). The resulting suspension was stirred 1 h at r.t. under inert atmosphere. Intermediate 1 (440 mg, 1.53 mmol) was added portionwise and the suspension was stirred at 80° C. under inert atmosphere. After 4 hours the reaction was cooled down to r.t. and quenched by addition of water. The solvents were evaporated and the residue was taken up in water. 2 mL of EtOAc and cyclohexane were added to trap the residual oil from NaH and the solution was stored at 4° C. for a day. The precipitate formed was filtered off and washed with water until neutral pH then with cyclohexane, affording 542 mg of crude base.

The crude base was taken up in MeOH (5 ml) and 100 μl of methane sulfonic acid was added. The salt precipitated and was filtered off then washed with ether and dried under vacuum at 30° C. to afford 642 mg (Yield=43%) of the title compound as a yellow powder. Y=43%; M⁻(ES): 443.0; M⁺(ES): 445.2; HPLC (Conditions b, max plot) 98.8%; Rt 2.22 min. ¹H NMR (DMSO-d6) δ 8.47-8.43 (m, 2H), 8.32 (br d, 1H), 8.00 (br d, 1H), 7.95 (d, J=7.9 Hz, 1H), 7.73 (d, J=7.9 Hz, 1H), 7.47-7.42 (m, 1H), 7.32-7.27 (m, 1H), 6.80 (br d, 1H), 5.77 (s, 2H), 3.76-3.73 (m, 4H), 3.40-3.37 (m, 4H), 2.33 (s, 6H).

Example 11

1,3-benzothiazol-2-yl[2-({3-[(4-methylpiperazin-1-yl)methyl]benzyl}oxy)pyrimidin-4-yl]acetonitrile

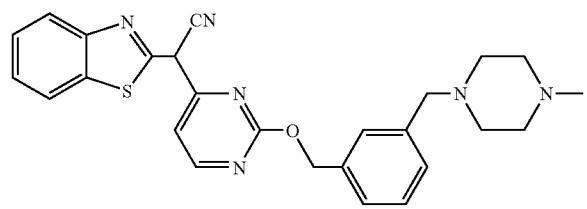

The title compound was obtained by performing the same protocol set out in the above Example 10, whereby {3-[(4-methylpiperazin-1-yl)methyl]phenyl}methanol is used instead of (3-morpholin-4-ylphenyl)methanol. Y=43%; M⁻(ESI): 469.0; M⁺(ESI): 471.2; HPLC (Conditions b, max plot) 96.7%; Rt 2.49 min. ¹H NMR (DMSO-d6) δ 7.94 (d, J=7.9 Hz, 1H), 7.88 (br s, 1H), 7.74 (br d, 1H), 7.54-7.52 (m, 2H), 7.46-7.35 (m, 3H), 7.28-7.23 (m, 1H), 6.71 (br d, 1H), 5.68 (s, 2H), 3.72 (br s, 2H), 3.50-3.40 (m, 8H), 2.75 (s, 3H).

Example 12

1,3-benzothiazol-2-yl(2-{[4-(3,4-dihydroisoquinolin-2(1H)-ylmethyl)benzyl]oxy}pyrimidin-4-yl)acetonitrile

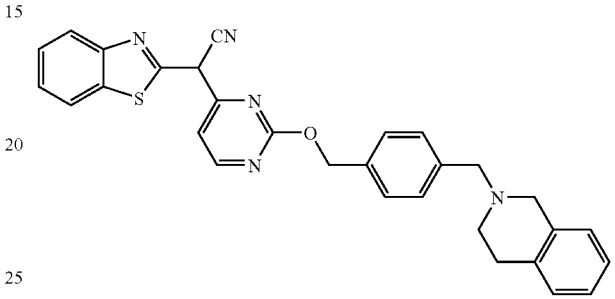

The title compound was obtained by performing the same protocol set out in the above Example 10, whereby [4-(3,4-dihydroisoquinolin-2(1H)-ylmethyl)phenyl]methanol is used instead of (3-morpholin-4-ylphenyl)methanol.

Y=30%; M⁻(ESI): 503.0; HPLC (Conditions b, max plot) 100%; Rt 3.11 min. ¹H NMR (DMSO-d₆) δ 710.13 (very br s, 1H), 7.95-7.92 (m, 2H), 7.74-7.72 (m, 2H), 7.69 (d, J=7.9 Hz, 2H), 7.61 (d, J=7.9 Hz, 2H), 7.45-7.40 (m, 1H), 7.28-7.22 (m, 4H), 7.10-7.07 (m, 1H), 6.72 (br d, 1H), 5.75 (s, 2H), 4.54 (s, 2H), 4.40-4.24 (m, 2H), 3.70-3.58 (m, 1H), 3.42-3.24 (m, 1H), 3.12-2.99 (m, 2H). CHN analysis: C₃₀H₂₅N₅OS. 2C₂HF₃O₂.1H₂O Calculated: C, 54.47%; H, 3.90%; N, 9.34%. Found: C, 54.36%; H, 4.01%; N, 8.93%.

Example 13

1,3-benzothiazol-2-yl[2-(hexyloxy)pyrimidin-4-yl]acetonitrile

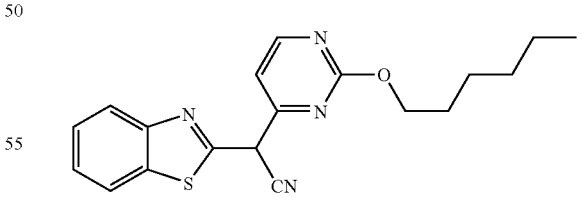

The title compound was obtained by performing the same protocol set out in the above Example 10, whereby hexan-1-ol is used instead of (3-morpholin-4-ylphenyl)methanol. Y=11%; M⁻(ESI): 350.6; M⁺(ESI): 353.2; HPLC (Conditions a, max plot) 98.1%; Rt 6.60 min. ¹H NMR (DMSO-d₆) δ 12.56 (br s, 1H), 7.85 (br d, 1H), 7.72-7.69 (m, 2H), 7.38-7.33 (m, 1H), 7.23-7.18 (m, 1H), 6.56 (br d, 1H), 4.60 (br t, 2H), 1.1.80-1.76 (m, 2H), 1.50-1.20 (m, 6H), 0.83 (br t, 3H).

Example 14

1,3-benzothiazol-2-yl(2-{[3-(morpholin-4-ylmethyl)benzyl]oxy}pyrimidin-4-yl)acetonitrile

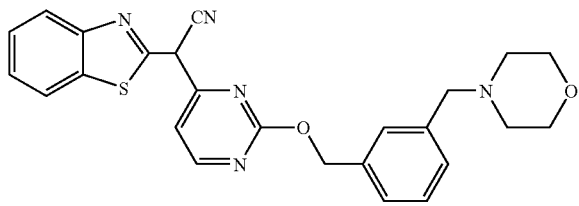

The title compound was obtained by performing the same protocol set out in the above Example 10, whereby (3-morpholin-4-ylmethyl-phenyl)methanol is used instead of (3-morpholin-4-ylphenyl)methanol. Y=72%; M$^-$(ESI): 456.0; M$^+$(ESI): 458; HPLC (Conditions b, max plot): 99.6%, rt. 2.35 min. $^1$H NMR (DMSO-d6) δ 9.92 (br s, 1H), 7.93-7.91 (m, 2H), 7.74-7.65 (m, 3H), 7.59-7.49 (m, 2H), 7.45-7.40 (m, 1H), 7.29-7.24 (m, 1H), 6.74 (br d, 1H), 5.72 (s, 2H), 4.05-3.75 (m, 2H), 3.65-3.50 (m, 2H), 3.30-3.02 (m, 4H). CHN analysis: $C_{25}H_{23}N_5O_2S$. 2 $C_2HF_3O_2$.1$H_2O$ Calculated: C, 49.50%; H, 3.87%; N, 9.95%. Found: C, 49.81%; H, 3.87%; N, 9.96%.

Example 15

1,3-benzothiazol-2-yl(2-{[3-(1H-imidazol-1-ylmethyl)benzyl]oxy}pyrimidin-4-yl)acetonitrile

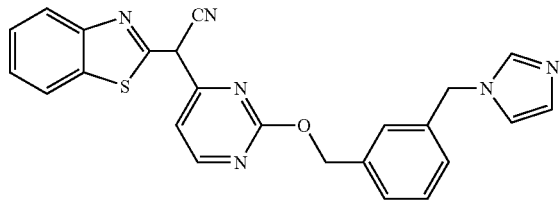

The title compound was obtained by performing the same protocol set out in the above Example 10, whereby (3-imidazolyl-1-ylmethyl-phenyl)methanol is used instead of (3-morpholin-4-ylphenyl)methanol. Y=41%; M$^-$(ES): 437.2; M$^+$(ES): 439.0; HPLC (Conditions b, max plot) 100%; Rt 2.41 min. $^1$H NMR (DMSO-d$_6$) δ 9.26 (s, 1H), 7.93-7.84 (m, 2H), 7.78 (t, J=1.5 Hz, 1H), 7.76 (d, J=7.9 Hz, 1H), 7.67 (t, J=1.5 Hz, 1H), 7.61-7.58 (m, 2H), 7.52-7.47 (m, 1H), 7.44-7.39 (m, 2H), 7.28-7.23 (m, 1H), 6.72 (br d, 1H), 5.67 (s, 2H), 5.47 (s, 2H).

Example 16

1,3-benzothiazol-2-yl(2-{[3-(piperidin-1-ylmethyl)benzyl]oxy}pyrimidin-4-yl)acetonitrile

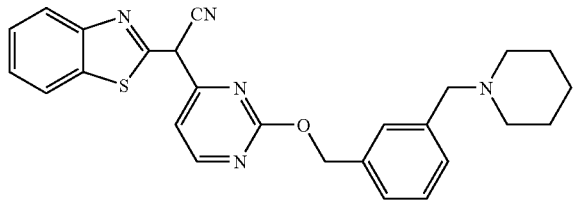

The title compound was obtained by performing the same protocol set out in the above Example 10, whereby (3-piperidin-1-ylmethyl-phenyl)methanol is used instead of (3-morpholin-4-ylphenyl)methanol. Y=35%; M$^-$(ES): 454.4; M$^+$(ES): 456.5; HPLC (Conditions b, max plot) 91.3%; Rt 2.50 min. $^1$H NMR (DMSO-d$_6$) δ 9.35 (br s, 1H), 7.93-7.91 (m, 2H), 7.74-7.64 (m, 3H), 7.58-7.50 (m, 2H), 7.48-7.40 (m, 1H), 7.28-7.23 (m, 1H), 6.73 (br d, 1H), 5.73 (s, 2H), 4.53 (s, 2H), 3.30-3.26 (m, 2H), 2.87-2.83 (m, 2H), 1.75-1.49 (m, 5H), 1.29-1.16 (m, 1H).

Example 17

1,3-benzothiazol-2-yl[2-({4-[(2,6-dimethylmorpholin-4-yl)methyl]benzyl}oxy)pyrimidin-4-yl]acetonitrile

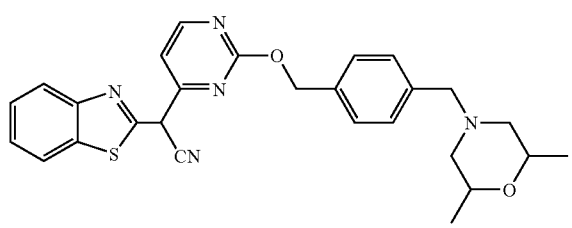

The title compound was obtained by performing the same protocol set out in the above Example 10, whereby (4-(2,6-dimethyl-morpholin-4-ylmethyl)-phenyl)methanol is used instead of (3-morpholin-4-ylphenyl)methanol. Y=15%; M$^+$(ES): 486.2; HPLC (Conditions b, max plot): 99%, rt. 2.48 min. $^1$H NMR (DMSO-d6) δ 10.29 (very br s, 1H), 7.92-7.90 (m, 2H), 7.73 (d, J=7.9 Hz, 1H), 7.66 (d, J=7.9 Hz, 2H), 7.56 (d, J=7.9 Hz, 2H), 7.44-7.39 (m, 1H), 7.28-7.23 (m, 1H), 6.72 (br d, 1H), 5.73 (s, 2H), 4.33 (s, 2H), 3.78-3.73 (m, 2H), 3.23 (d, J=11.7 Hz, 2H), 2.66 (t, J=11.7 Hz, 2H), 1.07 (s, 3H), 1.04 (s, 3H). CHN analysis: $C_{27}H_{27}N_5O_2S$. 2 $C_2HF_3O_2$.1.2$H_2O$ Calculated: C, 50.64%; H, 4.30%; N, 9.52%. Found: C, 50.98%; H, 4.80%; N, 9.68%.

Example 18

1,3-benzothiazol-2(3H)-ylidene{2-[(4-{[bis(2-methoxyethyl)amino]methyl}benzyl)oxy]pyrimidin-4-yl}acetonitrile

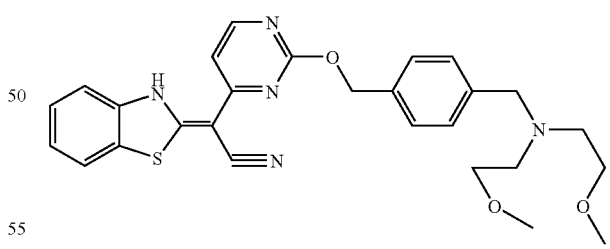

The title compound was obtained by performing the same protocol set out in the above Example 10, whereby (4-((bis-(2-methoxy-ethyl)-amino)-methyl)-phenyl)methanol is used instead of (3-morpholin-4-ylphenyl)methanol. Y=7%; M$^+$(ES): 504.2; HPLC (Conditions b, max plot): 99%, rt. 2.51 min. $^1$H NMR (DMSO-d6) δ 9.59 (br s, 1H), 7.94 (d, J=7.9 Hz, 1H), 7.88 (br d, 1H), 7.73 (d, J=8.2 Hz, 1H), 7.66 (d, J=8.3 Hz, 2H), 7.60 (d, J=8.3 Hz, 2H), 7.44-7.40 (m, 1H), 7.28-7.23 (m, 1H), 6.72 (br d, 1H), 5.73 (s, 2H), 4.40 (s, 2H), 3.65-3.63 (m, 4H), 3.33-3.21 (m, 10H). CHN analysis: $C_{27}H_{29}N_5O_3S$. 2

C₂HF₃O₂. Calculated: C, 50.89%; H, 4.27%; N. 9.57%. Found: C, 50.98%; H, 4.48%; N, 9.83%.

Example 19

1,3-benzothiazol-2(3H)-ylidene[2-({4-[(4-tert-butoxypiperidin-1-yl)methyl]benzyl}oxy)pyrimidin-4-yl]acetonitrile

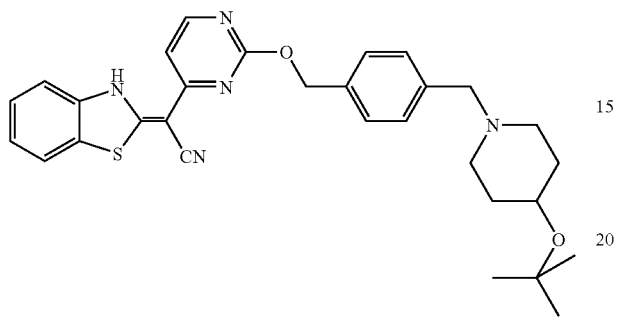

The title compound was obtained by performing the same protocol set out in the above Example 10, whereby (4-(4-tert-butoxy-piperidin-1-ylmethyl)-phenyl)methanol is used instead of (3-morpholin-4-ylphenyl)methanol. Y=66%; M⁻(ES): 526.3; M⁺(ES): 528.2; HPLC (Conditions b, max plot) 99.2%; Rt 2.93 min. ¹H NMR (DMSO-d₆) δ 9.38-9.29 (m, 1H), 7.93-7.91 (m, 2H), 7.73 (d, J=7.9 Hz, 1H), 7.67-7.63 (m, 2H), 7.58 (d, J=8.3 Hz, 1H), 7.53 (d, J=8.3 Hz, 1H), 7.44-7.39 (m, 1H), 7.28-7.23 (m, 1H), 6.73 (br d, 1H), 5.73 (s, 2H), 4.35-4.28 (m, 2H), 3.95-3.85 (m, 1H), 3.32-2.97 (m, 4H), 1.88-1.42 (m, 4H), 1.12 (d, J=7.6 Hz, 9H). CHN analysis: C₃₀H₃₃N₅O₂S. 2 C₂HF₃O₂.0.6H₂O Calculated: C, 53.27%; H, 4.76%; N, 9.14%. Found: C, 53.27%; H, 4.96%; N, 9.23%.

Example 20

1,3-benzothiazol-2-yl[2-({4-[(benzylamino)methyl]benzyl}oxy)pyrimidin-4-yl]acetonitrile

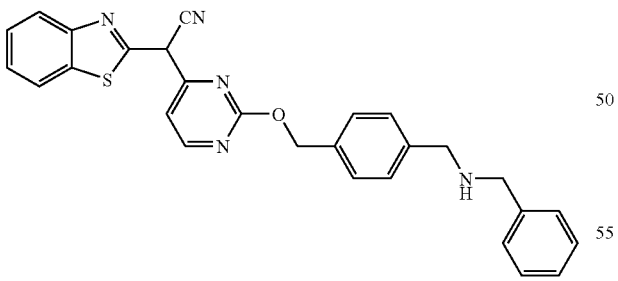

The title compound was obtained by performing the same protocol set out in the above Example 10, whereby benzyl-(4-hydroxymethyl-benzyl)-carbamic acid tert-butyl ester is used instead of (3-morpholin-4-ylphenyl)methanol. The Boc deprotection step was performed using the protocol described below.

To a solution of the crude base (0.5 g, 0.9 mmol) in DCM (18 ml) under inert atmosphere was added boron trifluoride diethyletherate (0.33 ml, 2.6 mmol) and the solution was stirred 1 h at r.t. Water was added to the reaction mixture and the organic phase was discarded. The precipitate formed in the aqueous phase was filtered off and taken up in MeOH. The insoluble material was removed by filtration and the filtrate was concentrated to near dryness at r.t. The residue obtained was purified by preparative HPLC. The pure fractions were gathered and lyophilised affording 0.055 g (11%) of the title compound as a yellow powder. Y=11%; M⁻(ES): 476.2; M⁺(ES): 478.2; HPLC (Conditions b, max plot) 97.5%; Rt 2.75 min. ¹H NMR (DMSO-d₆) δ 9.22 (br s, 1H), 7.94 (d, J=7.5 Hz, 1H), 7.73 (br d, 1H), 7.63 (br d, 2H), 7.54 (d, J=8.3 Hz, 2H), 7.46-7.39 (m, 7H), 7.28-7.23 (m, 1H), 6.72 (br d, 1H), 5.73 (s, 2H), 4.20-4.16 (m, 4H).

Example 21

1,3-benzothiazol-2-yl{2-[(2-morpholin-4-ylpyridin-4-yl)methoxy]pyrimidin-4-yl}acetonitrile

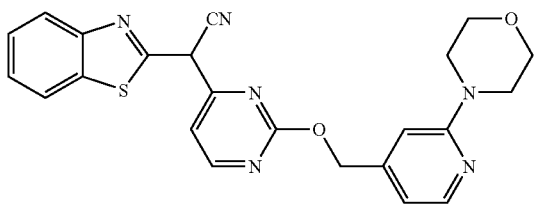

The title compound was obtained by performing the same protocol set out in the above Example 10, whereby N-(4-hydroxymethylpyridin-2-yl)morpholine is used instead of (3-morpholin-4-ylphenyl)methanol. Y=16%; M⁻(ES): 443.0; M⁺(ES): 445.0; HPLC (Conditions b, max plot) 94.4%; Rt 2.23 min. ¹H NMR (DMSO-d₆) δ 8.10 (d, J=6.4 Hz, 1H), 7.99-7.96 (m, 2H), 7.73 (d, J=7.9 Hz, 1H), 7.51-7.42 (m, 2H), 7.32-7.27 (m, 1H), 7.07 (br d, 1H), 6.78 (br d, 1H), 5.75 (s, 2H), 3.73-3.65 (m, 8H).

Example 22

1,3-benzothiazol-2-yl{2-[(2-piperidin-1-ylpyridin-4-yl)methoxy]pyrimidin-4-yl}acetonitrile

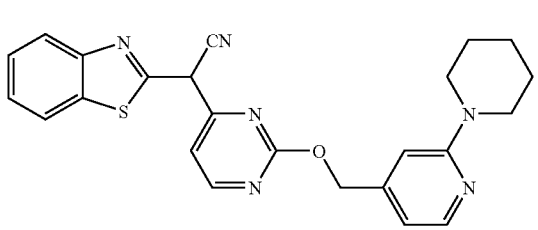

The title compound was obtained by performing the same protocol set out in the above Example 10, whereby (2-piperidin-1-yl pyridin-4-yl)methanol is used instead of (3-morpholin-4-ylphenyl)methanol. Y=39%; M⁻(ES): 441.1; M⁺(ES): 443.6.2; HPLC (Conditions b, max plot) 100%; Rt 2.60 min. ¹H NMR (DMSO-d6) δ 8.05-8.01 (m, 2H), 7.98 (d, J=7.9 Hz, 1H), 7.73 (d, J=7.9 Hz, 1H), 7.61 (s, 1H), 7.48-7.43 (m, 1H), 7.34-7.29 (m, 1H), 7.04 (br d, 1H), 6.83 (br d, 1H), 5.76 (s, 2H), 3.72-3.62 (m, 4H), 2.37 (s, 6H), 1.70-1.54 (m, 6H).

Example 23

1,3-benzothiazol-2-yl[2-(2-morpholin-4-ylethoxy)pyrimidin-4-yl]acetonitrile

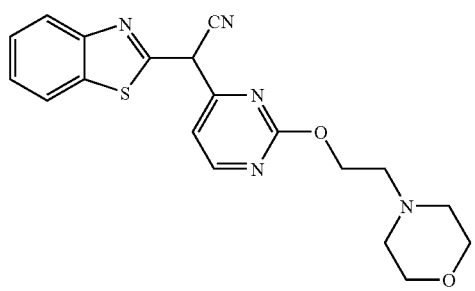

The title compound was obtained by performing the same protocol set out in the above Example 10, whereby 4-(2-hydroxyethyl)morpholine is used instead of (3-morpholin-4-ylphenyl)methanol. Y=72%; M$^-$(ES): 380.2; HPLC (Conditions b, max plot): 100%, rt. 1.86 min. $^1$H NMR (DMSO-d6) δ 10.28 (very br s, 1H), 7.99 (br d, 1H), 7.88 (d, J=7.9 Hz, 1H), 7.72 (d, J=7.9 Hz, 1H), 7.47-7.42 (m, 1H), 7.32-7.27 (m, 1H), 6.78 (br d, 1H), 5.01-4.88 (m, 2H), 4.15-3.10 (m, 8H), 3.76-3.65 (m, 2H).

Example 24

1,3-benzothiazol-2(3H)-ylidene{2-[(1,4-dimethylpiperazin-2-yl)methoxy]pyrimidin-4-yl}acetonitrile

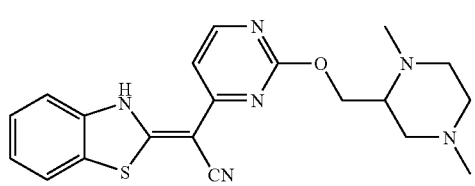

The title compound was obtained by performing the same protocol set out in the above Example 10, whereby 1,4-dimethyl-2-(hydroxymethyl)piperazine is used instead of (3-morpholin-4-ylphenyl)methanol. Y=36%; M$^+$(ES): 394.8; HPLC (Conditions b, max plot): 97.6%, rt. 1.67 min. $^1$H NMR (DMSO-d6) δ 8.00 (br d, 1H), 7.90 (d, J=7.9 HZ, 1H), 7.72 (d, J=7.9 Hz, 1H), 7.47-7.42 (m, 1H), 7.32-7.27 (m, 1H), 6.79 (br d, 1H), 4.84-4.70 (m, 2H), 3.62-3.58 (m, 1H), 3.45-3.41 (m, 1H), 3.25-3.07 (m, 4H), 2.90-2.70 (m, 1H), 2.81 (s, 3H), 2.62 (s, 3H).

Example 25

1,3-benzothiazol-2-yl{2-[2-(dimethylamino)ethoxy]pyrimidin-4-yl}acetonitrile

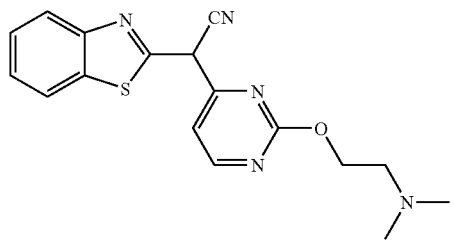

The title compound was obtained by performing the same protocol set out in the above Example 10, whereby 2-dimethylaminoethanol is used instead of (3-morpholin-4-ylphenyl)methanol. Y=66%; M$^+$(ES): 339.; HPLC (Conditions b, max plot): 100%, rt. 1.80 min. $^1$H NMR (DMSO-d6) δ 9.84 (br s, 1H), 8.00 (br d, 1H), 7.89 (d, J=7.9 HZ, 1H), 7.72 (d, J=7.9 Hz, 1H), 7.47-7.42 (m, 1H), 7.32-7.27 (m, 1H), 6.79 (br d, 1H), 4.96-4.86 (m, 2H), 3.70-3.60 (m, 2H), 2.91 (s, 3H).

Example 26

1,3-benzothiazol-2(3H)-ylidene[2-({4-[(4-methylpiperazin-1-yl)carbonyl]benzyl}oxy)pyrimidin-4-yl]acetonitrile

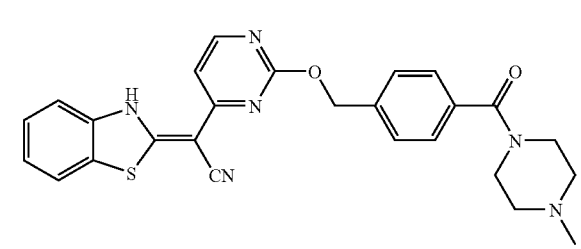

The title compound was obtained by performing the same protocol set out in the above Example 10, whereby {4-[(4-methylpiperazin-1-yl)carbonyl]phenyl}methanol is used instead of (3-morpholin-4-ylphenyl)methanol. Y=44%; M$^+$(ES): 485.5; HPLC (Conditions b, max plot): 100%, rt. 2.21 min. $^1$H NMR (DMSO-d6) δ 9.88 (br s, 1H), 7.93 (br d, 1H), 7.95-7.84 (very br d, 1H), 7.73 (br d, 1H), 7.67 (d, J=8.3 Hz, 2H), 7.52 (d, J=8.3 Hz, 2H), 7.45-7.39 (m, 1H), 7.28-7.23 (m, 1H), 6.73 (br d, 1H), 5.74 (s, 2H), 4.50-3.00 (m, 8H), 2.81 (s, 3H).

Example 27

1,3-benzothiazol-2-yl{2-[3-(dimethylamino)propoxy]pyrimidin-4-yl}acetonitrile

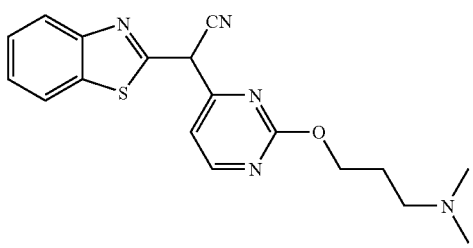

The title compound was obtained by performing the same protocol set out in the above Example 10, whereby 3-dimethylamino-1-propanol is used instead of (3-morpholin-4-yl phenyl)methanol. Y=65%; M$^+$(ES): 353.2; HPLC (Conditions b, max plot): 100%, rt. 1.77 min. $^1$H NMR (DMSO-d6) δ 9.46 (br s, 1H), 7.94-7.82 (m, 2H), 7.74 (br d, 1H), 7.46-7.41 (m, 1H), 7.31-7.26 (m, 1H), 6.70 (br d, 1H), 4.73-4.62 (m, 2H), 3.30-3.20 (m, 2H), 2.83-2.82 (m, 6H), 2.28-2.18 (m, 2H).

CHN analysis: $C_{18}H_{19}N_5OS \cdot 2\ C_2HF_3O_2 \cdot 1H_2O$ Calculated: C, 44.08%; H, 3.87%; N, 11.68%. Found: C, 43.71%; H, 4.01%; N, 11.67%.

Example 28

1,3-benzothiazol-2-yl{2-[2-(4-methylpiperazin-1-yl)ethoxy]pyrimidin-4-yl}acetonitrile

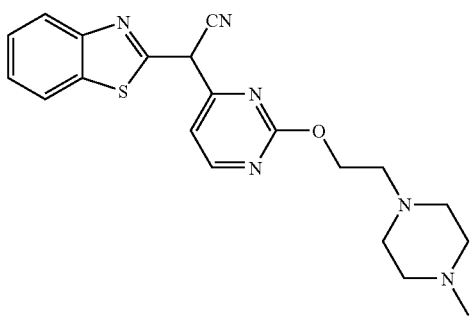

The title compound was obtained by performing the same protocol set out in the above Example 10, whereby 2-(4-methylpiperazin-1-yl)ethanol is used instead of (3-morpholin-4-ylphenyl)methanol. Y=7%; M$^-$(ES): 393.2; M$^+$(ES): 395.1; HPLC (Conditions b, max plot) 97.4%; Rt 1.64 min. $^1$H NMR (DMSO-d$_6$) δ 7.94-7.88 (m, 2H), 7.75 (d, J=7.9 Hz, 1H), 7.46-7.41 (m, 1H), 7.31-7.26 (m, 1H), 6.71 (br d, 1H), 4.83 (br t, 2H), 3.58-3.05 (m, 8H), 2.92-2.68 (m, 5H).

Example 29

1,3-benzothiazol-2-yl(2-{2-[2-(dimethylamino)ethoxy]ethoxy}pyrimidin-4-yl)acetonitrile

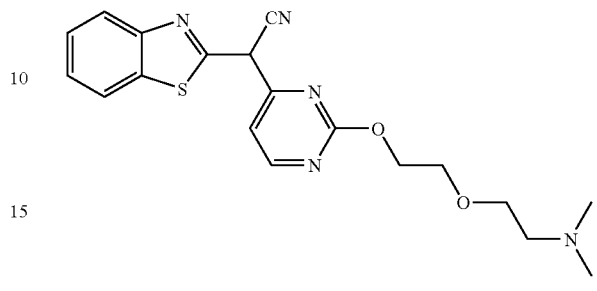

The title compound was obtained by performing the same protocol set out in the above Example 10, whereby 2-[2-(dimethylamino)ethoxy]ethanol is used instead of (3-morpholin-4-ylphenyl)methanol. Y=56%; M$^+$(ES): 384.2; HPLC (Conditions b, max plot): 99%, rt. 1.77 min. $^1$H NMR (DMSO-d6) δ 9.38 (br s, 1H), 7.99-7.97 (m, 1H), 7.95-7.93 (m, 1H), 7.77 (d, J=7.9 Hz, 1H), 7.50-7.45 (m, 1H), 7.36-7.30 (m, 1H), 6.78 (br d, 1H), 4.86-4.77 (m, 2H), 3.98-3.91 (m, 2H), 3.84-3.81 (m, 2H), 3.33-3.28 (m, 2H), 2.81-2.80 (m, 6H), 2.38 (s, 6H).

Example 30

Figure 5:
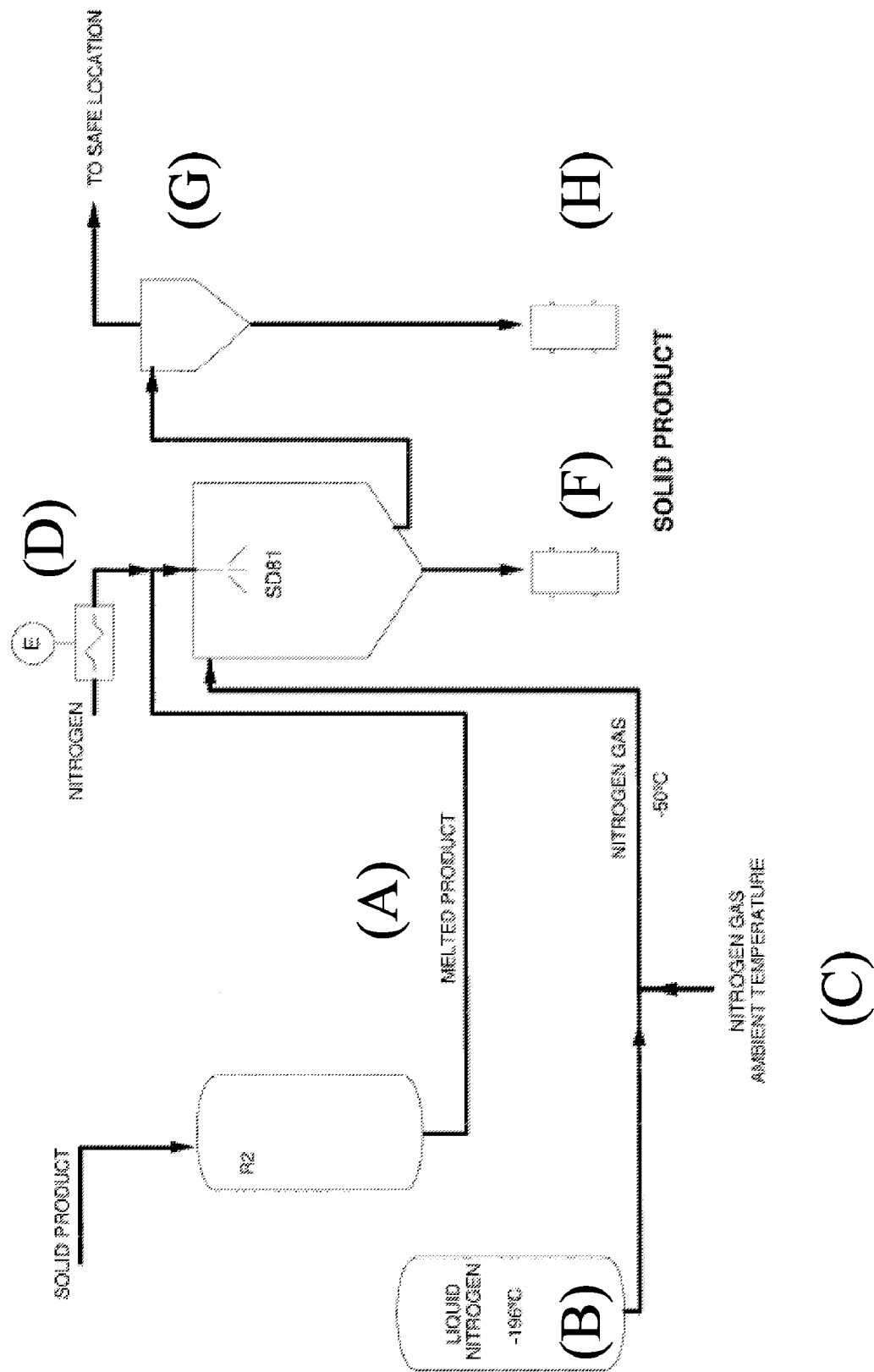
FIG. 5 represents a spray chilling unit wherein (R2) represents a thermostated water bath, SD81 is the cooling chamber, (A) represents the suspension feeding pipes, (B) the liquid nitrogen source, (C) the nitrogen gas, (D) the atomising nitrogen, (F) the primary product collection chamber, (H), the secondary product collection chamber and (G) the cyclone.

Preparation of Benzothiazole Macrogol Glyceride Formulations (2) and (6) by Spray Chilling 1. General Preparation Procedure A suitable amount of Gelucire in powder form was melted in a thermostated water bath (R2) (FIG. 5). A suitable amount of benzothiazole (Compound A) in powder form, optionally micronized by air-jet milling, (40% w/w calculated on the total composition for formulation (2) and 30% w/w calculated on the total composition for formulation (6)) was dispersed into the molten excipient. The mass was kept under stirring for about 30 min, until a homogeneous dispersion was obtained. The benzothiazole-loaded Gelucire was then stirred for 5 minutes using a homogenizer (IKA, model T25-basic Turrax®) at maximum speed (24000 rpm) before being transferred to the reactor (R2). The excipient/suspension was maintained in the reactor (R2) under stirring at a temperature of about 80° C. The temperature was controlled by a Digiterm 2 000 heater and monitored with a thermometer.

The benzothiazole-loaded Gelucire was transferred from the reactor (R2) to the cooling chamber SD81 by pressurizing the vessel, preferably at 100 mbar or more through the feeding pipes (A) that are maintained at a temperature sufficient to avoid the cooling of the suspension inside the pipes. Alternatively, a peristaltic pump can be used to transfer the suspension from the reactor to the cooling chamber SD81.

The benzothiazole-loaded Gelucire was then introduced in the cooling chamber SD81 through a nozzle under nitrogen flux (atomizing nitrogen), preferably between 50-80° C. An electric resistance is used in order to ensure the adequate temperature of the atomizing nitrogen as a preferred alternative to the passage of the gas through a coil place in a warmed bath to be heated.

Cold nitrogen gas (nitrogen for congealing) obtained by mixing nitrogen evaporated from a liquid nitrogen source (B)

with nitrogen gas at room temperature (C) is flushed into the cooling chamber SD81, at a temperature between −50° C. and +20° C., but preferably at a temperature between −30° C. and +10° C.

All piping for nitrogen circulation was carefully lagged to minimize heat exchange with the exterior and help to maintain the set temperatures.

The inlet and outlet temperatures of the cooling chamber SD81 were monitored by Pt100 sensors. The temperature of the nozzle is preferably held above 50° C. to avoid any blockage.

The distance between reactor and nozzle should be minimal to reduce pressure drop in the feed line.

Larger nozzles (orifice 1.4 mm/cap 2.2 mm) are preferably used for suspension with higher viscosity such as suspension for the preparation of formulation (2).

The so-obtained particles or pellets are collected in F and then in H after separation from the gas flow in cyclone G.

2. Benzothiazole 1,3 benzothiazol-2-yl-[2-(4-morpholin-4-ylmethyl-benzyloxy)-pyrimidin-4-yl]-acetonitrile, (Compound A) was synthesized as described in Example 1 of WO 03/047570. Compound A is used as a mesylate salt form having a molecular weight of 649.75 Da, with a salt/base ratio of 1.42 (the molecular weight of Compound A as a free base is 457.55 Da).

3. Excipients:

Gelucire 50/13 (Stearoyl macrogol-32 glycerides) is as described in Example 1.

4. Macrogol Glyceride Compositions (2) and (6)

Stearoyl macrogol glyceride pellets composition (2) has the same composition as in Example 2. Stearoyl macrogol glyceride pellets composition (6) has following composition:

| | |
|---|---|
| Compound A (mesylate salt) | 30% w/w |
| Gelucire 50/13 | 70% w/w |

Compositions (2) and (6) were manufactured according to the general procedure above.

For composition (2), 80 g of powder of Compound A and 120 g of powder of Gelucire 50/13, respectively were used and melting of the Gelucire matrix was performed in a thermostated bath at 60° C.

For composition (6), 30 g of powder of Compound A and 70 g of powder of Gelucire 50/13, respectively were used and melting of the Gelucire matrix was performed in a thermostated bath at 60° C.

The yields of the process were 64% and 55% for compositions (2) and (6), respectively.

5. Physico-Chemical Characteristics 5.1. Drug Content

Drug content was measured by RP-HPLC (37.6% for composition (2) obtained by spray chilling).

5.2. Thermal Analysis

Thermal analysis was performed by DSC analysis and X-ray powder diffraction.

5.4. Particle Morphology

The morphology of the particles of compositions (2) and (6) obtained by spray chilling was analysed by stereomicroscopy on dry material (STEMI 2000-C Carl Zeiss, magnification 16). The shape and size of the particles showed to be regular.

Figure 7:
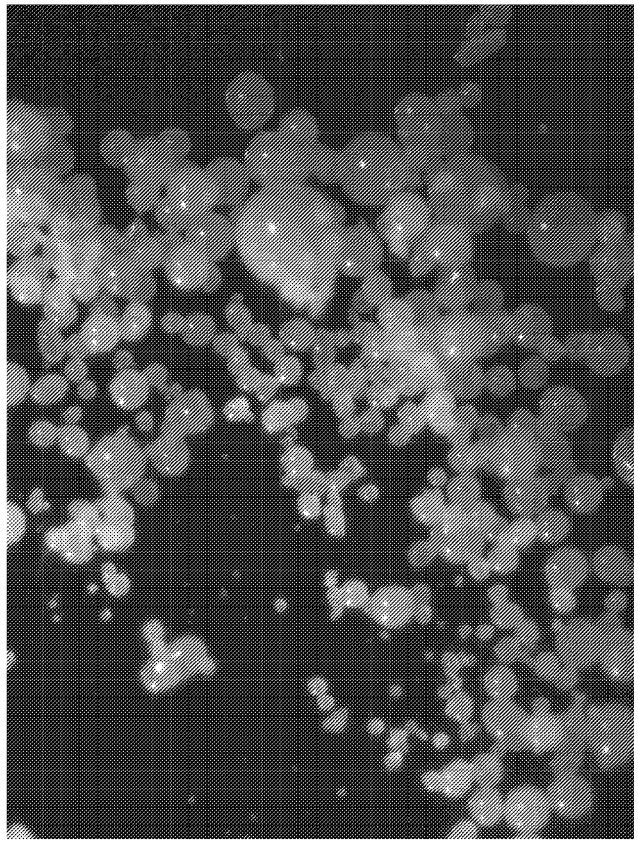
FIG. 7 represents the stereomicroscopy images of formulations (2) and (6) prepared by spray chilling.
Figure 7:
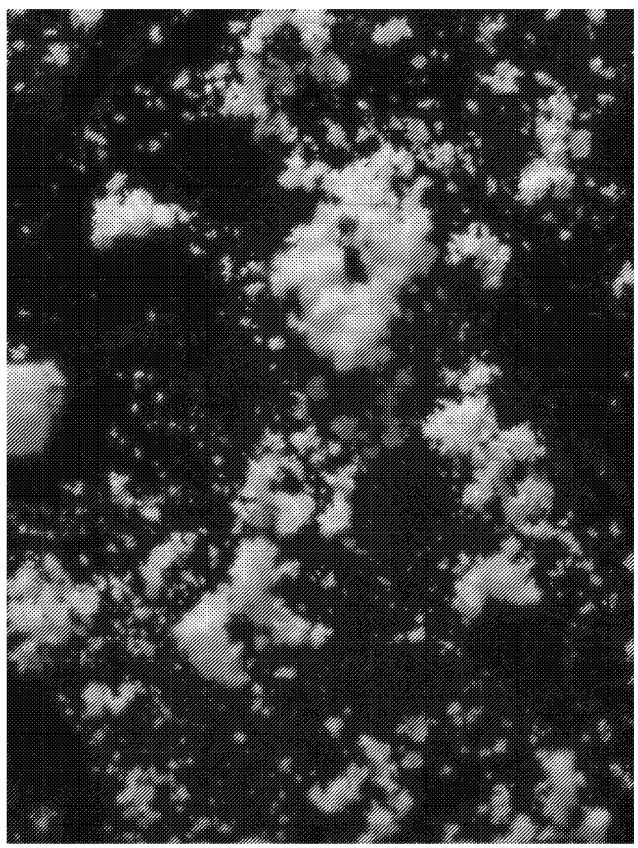

The particles of composition (2) obtained by spray chilling exhibited improved regularity in terms of shape and size as compared to the particles of same composition (2) obtained by a process according to Example 2, before grinding (FIG. 7).

This shows that the method according to Example 30 provides regular particles without the need of a grinding step.

5.5. In Vitro Dissolution Test

Solubilization tests analysis of composition (2) was performed using a dissolution tester with USP II apparatus (paddle). Dissolution medium was FeSSIF (Fed State Simulated Intestinal Fluid, without lecithin) and rotation speed was kept at 75 rpm.

Figure 6:
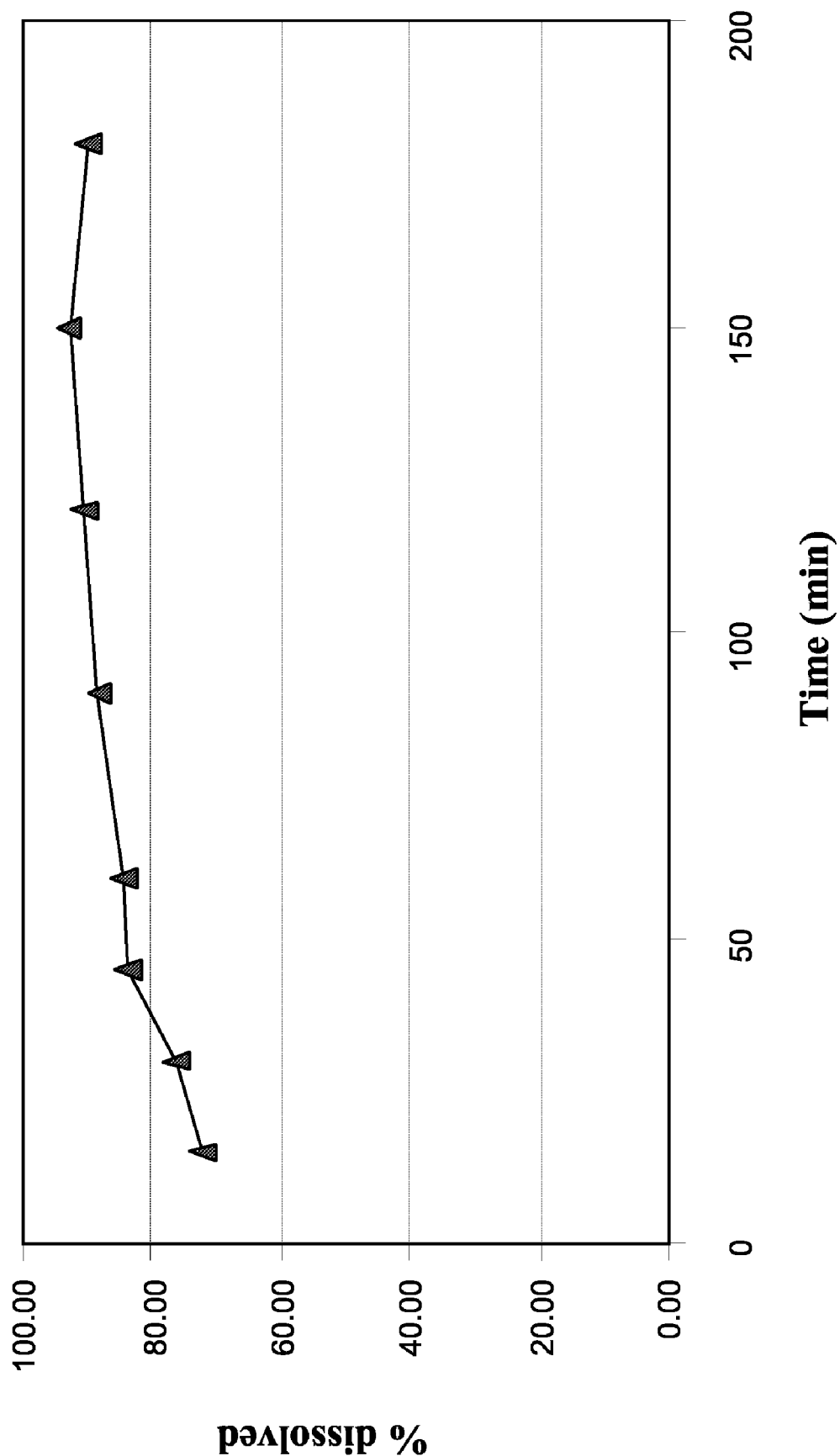
FIG. 6 represents the solubilization profile (expressed as dissolved percentage versus time (min)) in oversaturation conditions, Fed State Simulated Intestinal Fluid (FeSSIF), without lecithin as dissolution medium) of Compound A in macrogol glyceride solid formulation (2) prepared by spray chilling (Filled triangles).

Dissolution rate profile was found to be very fast, with more than 80% of drug substance dissolved after 1 hour (FIG. 6) and improved compared to bulk.

Example 31

Experimental Allergic Encephalomyelitis (EAE) Model

Compounds and/or formulations according to the invention can be evaluated for their activity in a model for multiple sclerosis in mice.

Animals

C57BL/6NCrlBR female mice are used. Mice are kept in wire cages (cm 32×14×13 h) with stainless steel feeders and fed on a standard diet (4RF21, Charles River, Italy) and water ad libitum. From day 7, wet pellets are also placed every day on the bottom of the cage. Plastic bottles are used in addition to the automatic water system.

Experimental Procedure

Mice are immunized (day=0) by injecting s.c. in the left flank 0.2 ml of an emulsion composed of 200 µg $MOG_{35-55}$ peptide (Neosystem, Strasbourg, France) in Complete Freund's Adjuvant (CFA, Difco, Detroit, U.S.A.) containing 0.5 mg of *Mycobacterium tuberculosis*. Immediately after, they receive an i.p. injection of 500 ng pertussis toxin (List Biological Lab., Campbell, Calif., U.S.A.) dissolved in 400 µL of buffer (0.5 M NaCl, 0.017% Triton X-100, 0.015 M Tris, pH=7.5). On day 2, the animals are given a second injection of 500 ng pertussis toxin.

On day 7, the mice receive a second dose of 200 µg of $MOG_{35-55}$ peptide in CFA injected s.c. in the right flank. Starting approximately from day 8-10, this procedure results in a progressing paralysis, arising from the tail and ascending up to the forelimbs.

Animals are individually weighed and are examined for the presence of paralysis that is scored according to the following score-system (1):

0=no signs of disease
0.5=partial tail paralysis
1=tail paralysis
1.5=tail paralysis+partial unilateral hindlimb paralysis
2=tail paralysis+bilateral hindlimb weakness or partial paralysis
2.5=tail paralysis+partial hindlimb paralysis (lowered pelvi)
3=tail paralysis+complete hindlimb paralysis
3.5=tail paralysis+hindlimb paralysis+incontinence
4=tail paralysis+hindlimb paralysis+weakness or partial paralysis of forelimbs
5=moribund or dead Mortality and clinical signs are monitored daily in each group of treatment, by a technician who is unaware of treatments.

Daily treatment with compounds, their vehicle or with a reference compound starts on day 7 and continued for 15 or 21 consecutive days in all groups.

Histopathological Examination

At the end of the treatment period, each animal is anesthetised with sodium pentobarbital and is transcardially perfused-fixed with 4% paraformaldehyde via the left ventricle. Fixed spinal cords are then carefully dissected out.

Spinal cord slices are embedded in paraffin blocks. Sectioning and staining with hematoxylin and eosin and CD45 staining for inflammation, and with Kluver-PAS (Luxol fast blue plus Periodic Acid Schiff staining) and Bielchowski's staining for the detection of demyelination and axonal loss, are performed.

In the spinal cord, the total area of all slices is measured for each animal as points of intersection of a 10×10 grid at a magnification of 0.4×0.4 mm per grid. The perivascular inflammatory infiltrates are counted in each slice in order to obtain a total value for each animal and evaluated as number of infiltrates per $mm^2$. Demyelination and axonal loss areas are measured for each animal as points of intersection of 10×10 grid at a magnification of 0.1×0.1 mm per grid and are expressed as a percentage of total demyelination area over the total area of the slices.

Data Evaluation and Statistical Analysis

The results of clinical and histopathological observations are expressed as the mean (±SEM) scores in each treatment group. Values obtained in the test drug-treated groups are compared with that of the positive control group. Significance of differences among groups relating to clinical score are analysed by one-way ANOVA, followed in case of significance ($p<0.05$) by Fisher test.

Differences among groups for the presence of perivascular inflammatory infiltrates and the extent of demyelination and axonal loss in the spinal cord as well as body weight data are analysed by one-way ANOVA, followed in case of significance ($p<0.05$) by Fisher test.

Example 32

Asthma Model

Compounds and/or formulations according to the invention can be evaluated for their activity in a model of diseases associated with lung inflammation, such as asthma.

The effect of the compounds and/or compositions of the invention on the airway responsiveness in response to methacholine-challenge, airway inflammation, eosinophilia and mucus production can be observed. The effect of the compounds and/or compositions of the invention on IL-2 and IFN-g produced by pulmonary lymphocytes recovered by BAL can be also observed in this model.

Balb/c mice are immunised with 10 mg of ovalbumin (OVA) in 0.2 ml of alum, administered i.p. 14 days later, Compounds or formulations according to the invention (20, 45, 70 and 100 mg/kg) or vehicle (0.9% NaCl) was administered p.o. 1 h before and 4 h after OVA-challenge via the intranasal route. This procedure is repeated daily for 5 days. Dexamethasone tested at 0.5 mg/kg may be used as a reference treatment. Control mice are saline-sensitised and challenged daily for 5 days with 0.9% NaCl alone.

Airway responsiveness is measured 24 h after the last OVA-challenge by recording respiratory pressure curves by whole body plethysmography in response to inhaled methacholine at $3\times10^{-2}$ M, monitored during a 15 minute period. This method allows measurements of spontaneous breathing in a non-restrained mouse inside a Plexiglas chamber. The airway reactivity is expressed as a variable known as enhanced pause (Penh), a calculated value that correlates with measurement of airway resistance, impedance, and intrapleural pressure in the same mouse. Penh=(Te/Tr−1)×Pef/Pif (Te, expiration time; Tr, relaxation time; Pef, peak expiratory flow; Pif, peak inspiratory flow).

Broncho Alveolar Lavage (BAL) is performed 72 h after OVA exposure. Following a total cell count, slides are prepared, stained, and differentiated as eosinophils, neutrophils, and mononuclear cells by counting a minimum of 200 cells per slide and expressing the results as numbers of each cell type.

Two days after the last challenge, mice are sacrificed. Lungs are gently inflated by instillation of OCT (Optimum cutting tissue) compound (TissueTeck, Miles Inc.), embedded in OCT, frozen and cryosectioned. Different stainings are performed: A) May-GrunWald-Giemsa to assess cell infiltration in blue, B) DiaminoBenzidine for eosinophil infiltration in brown and C) Alcian Blue/Periodic Acid Schiff's for mucus production in blue. Examination for histological changes of sections is performed by light microscopy. Pictures representative of a field are captured by microscopy.

Total leukocytes recovered from the airways by BAL are stimulated in vitro with anti-CD3 antibody for 48 h. Quantification of IL-4, IL-5, IL-2, IFN-g and TNF-a secreted in the supernatant is performed using the cytokine cytometric bead array (CBA) kit (BD PharMingen).

Example 33

Endometriosis Model

Compounds and/or formulations according to the invention can be evaluated for their activity in a model for endometriosis in mice or rats.

Mice Model:

Human endometrial tissue is injected in ovarectomized nude mice to establish the disease (Bruner-Tran et al., 2002, *Ann NY Acad Sci.*, 955:328-339).

Endometrial biopsies obtained from normal volunteers or from endometriotic patients are cut into small pieces and cultured in the presence of estradiol for 24 h. Treated tissues, are injected either subcutaenously or intraperitoneally into ovarectomized nude mice with estradiol implant. Within 2-4 days of injection, ectopic endometriotic lesions developed in animals. Treatment with either progesterone or a compound or fomulation of the invention inhibitor was started 10-12 days following the injection of tissue. The compound is administered at a dose of 10 mg/kg and 30 mg/kg/animal for 30 days. Earlier work using this model has established that progesterone treatment prevents disease progression, hence this is used as control. Following the completion of treatment, animals are sacrificed, lesions developed from the transplanted tissue found in both subcutaneous and intraperitoneal sites, are measured (both size and number). The effect of the compounds and/or formulation of the invention in regressing the established disease is evaluated.

Rat Model:

Endometriosis is induced in rats as described earlier (D'Antonio et al., 2000, *J. Reprod. Immunol.* 48:81-98).

In brief, autologous uterine horn fragment is transplanted onto the inner surface of the abdominal wall in rat. Three weeks following transplantation, the size and the viability of the engrafted tissue is measured. One week after the confirmation of the tissue attachment, treatments are started.

The control group received the vehicle only. The compound and/or formulations of the invention is administered orally (po) at doses of 10 mg/kg and 30 mg/kg per day.

Treatment with compound and/or formulations is conducted for nine days, animals are anaesthetized 2 hr following the last treatment and blood samples are collected. Surface area of the endometriosis-like foci is measured, endometriotic-like foci flushed with PBS and contralateral uterine flushing is also collected for measuring cytokine. The endometriotic-like foci and spleen is removed for histology and for NK cell activity measurement respectively.

The effect of the compounds and/or formulation of the invention in regressing the established disease is evaluated.

Example 34

Fibrosis Model

The compounds and/or formulations according to the may be subjected to the following assays in order to demonstrate their utility for the treatment of scleroderma and its therapeutic implications such as systemic sclerosis, scleroderma-like disorders or sine scleroderma.

Fibrosis models as described in WO 03/047570 can be used to determine the loss of body weight of mice which is usually triggered by bleomycin-induced lung fibrosis, to analyse focal fibrotic lesions that are histologically determined on day 17 after bleomycin administration, to specifically measure the hydroxyproline content in the lungs of bleomycin-treated mice.

The invention claimed is:

1. A pharmaceutical composition comprising a benzothiazole of Formula (I):

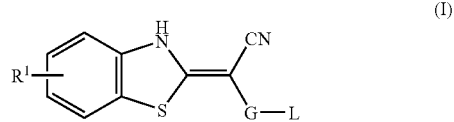

or tautomers, geometrical isomers, enantiomers, diastereomers or racemate forms, or the pharmaceutically acceptable salts thereof, wherein:
  G is a pyrimidinyl group;
  L is a alkoxy, amino group, or a 3-8 membered heterocycloalkyl, containing at least one heteroatom selected from nitrogen, oxygen and sulfur;
  R1 is selected from the group consisting of: hydrogen; sulfonyl; amino; C1-C6-alkyl; C2-C6-alkenyl; C2-C6-alkynyl; alkoxy; aryl; halogen; cyano; and hydroxy; and a macrogol glyceride.

2. The composition according to claim 1 wherein the macrogol glyceride is a stearoyl glyceride.

3. The composition according to claim 1 wherein the macrogol glyceride is Gelucire® 50/13 (stearoyl macrogol-32 glycerides).

4. The composition according to claim 3 wherein Gelucire® 50/13 (stearoyl macrogol-32 glycerides) is present in an amount of 40% w/w to 95% w/w, relative to the total composition.

5. The composition according to claim 3 wherein Gelucire® 50/13 (stearoyl macrogol-32 glycerides) is present in an amount of 40% w/w to 60% w/w, relative to the total composition.

6. The composition according to claim 1 wherein the benzothiazole of Formula I is present in an amount of 5% w/w to 40% w/w, relative to the total composition.

7. The composition according to claim 1 wherein the benzothiazole of Formula I is present in an amount of 20% w/w to 40% w/w relative to the total composition.

8. The composition according to claim 1 wherein the benzothiazole of Formula I is 1,3-benzothiazol-2-yl-[2-(4-morpholin-4-ylmethyl-benzyloxy)-pyrimidin-4-yl]-acetonitrile, or a pharmaceutically acceptable salt thereof.

9. The composition according to claim 8 wherein the benzothiazole is the mesylate salt of 1,3-benzothiazol-2-yl-[2-(4-morpholin-4-ylmethyl-benzyloxy)-pyrimidin-4-yl]-acetonitrile.

10. The composition according to claim 1, further comprising a poloxamer.

11. The composition according to claim 10, wherein the poloxamer is Poloxamer 188.

12. The composition according to claim 1, further comprising a Polyethylene Glycol.

13. The composition according to claim 1, wherein said composition comprises at least 20% w/w of the mesylate salt of 1,3-benzothiazol-2-yl-[2-(4-morpholin-4-ylmethyl-benzyloxy)-pyrimidin-4-yl]-acetonitrile and Gelucire® 50/13 (stearoyl macrogol-32 glycerides) in an amount of 40% w/w to 80% w/w, relative to the total composition.

14. A composition according to claim 1, wherein the composition is selected from the group consisting of:
  1,3-benzothiazol-2-yl-[2-(4-morpholin-4-ylmethyl-benzyloxy)-pyrimidin-4-yl]-acetonitrile, mesylate salt at 20% w/w and Gelucire® 50/13 (stearoyl macrogol-32 glycerides) at 80% w/w, relative to the total composition;
  1,3-benzothiazol-2-yl-[2-(4-morpholin-4-ylmethyl-benzyloxy)-pyrimidin-4-yl]-acetonitrile, mesylate salt at 40% w/w and Gelucire® 50/13 (stearoyl macrogol-32 glycerides) at 60% w/w, relative to the total composition;
  1,3-benzothiazol-2-yl-[2-(4-morpholin-4-ylmethyl-benzyloxy)-pyrimidin-4-yl]-acetonitrile, mesylate salt at 30% w/w and Gelucire® 50/13 (stearoyl macrogol-32 glycerides) at 70% w/w, relative to the total composition;
  1,3-benzothiazol-2-yl-[2-(4-morpholin-4-ylmethyl-benzyloxy)-pyrimidin-4-yl]-acetonitrile, mesylate salt at 20% w/w, Gelucire® 50/13 (stearoyl macrogol-32 glycerides) at 40% w/w, and Lutrol® F68 (polyoxyethylene-polyoxypropylene block copolymer) at 40% w/w, relative to the total composition;
  1,3-benzothiazol-2-yl-[2-(4-morpholin-4-ylmethyl-benzyloxy)-pyrimidin-4-yl]-acetonitrile, mesylate salt at 20% w/w, Gelucire® 50/13 (stearoyl macrogol-32 glycerides) at 40% w/w, and Lutrol® E6000 (polyethylene glycol) at 40% w/w, relative to the total composition; and
  1,3-benzothiazol-2-yl-[2-(4-morpholin-4-ylmethyl-benzyloxy)-pyrimidin-4-yl]-acetonitrile, mesylate salt at 5% w/w and Gelucire® 50/13 (stearoyl macrogol-32 glycerides) at 95% w/w, relative to the total composition.

15. A method of treating a patient having a disorder selected from multiple sclerosis, asthma, scleroderma and endometriosis, comprising administering to the patient in need thereof, an effective amount of a pharmaceutical composition according to claim 1 to treat a disorder selected from multiple sclerosis, asthma, scleroderma and endometriosis.

16. A process for the manufacture of a pharmaceutical composition, wherein said process comprises adding a benzothiazole according to Formula (I) to a molten preparation of macrogol glyceride;

wherein:

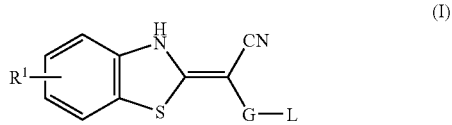

G is a pyrimidinyl group;
L is a alkoxy, amino group, or a 3-8 membered heterocycloalkyl, containing at least one heteroatom selected from nitrogen, oxygen and sulfur; and
R1 is selected from the group consisting of: hydrogen; sulfonyl; amino; C1-C6-alkyl; C2-C6-alkenyl; C2-C6-alkynyl; alkoxy; aryl; halogen; cyano; and hydroxy.

17. The process according to claim 16, wherein the benzothiazole is added into the macrogol glyceride molten preparation in a powder form under stirring, thus resulting in a homogenous molten dispersion.

18. The process according to claim 17, further comprising the steps of:
a) cooling down the homogenous molten dispersion; and
b) grinding the resultant solid into particles.

19. The process according to claim 18, wherein the cooling down step comprises atomization under CO2.

20. The process according to claim 18, wherein the process further comprises a freeze-drying step after the grinding step.

21. The process according to claim 17, wherein the resultant homogenous molten dispersion is subsequently cooled down by spray chilling.

22. The process according to claim 16 wherein the benzothiazole is added into the macrogol glyceride molten preparation in a water solution form under stirring.

* * * * *